US010192044B2

(12) United States Patent
Choe et al.

(10) Patent No.: US 10,192,044 B2
(45) Date of Patent: Jan. 29, 2019

(54) ELECTRONIC APPARATUS AND METHOD FOR CONTROLLING FUNCTIONS IN THE ELECTRONIC APPARATUS USING A BIO-METRIC SENSOR

(71) Applicant: Samsung Electronics Co., Ltd., Gyeonggi-do (KR)

(72) Inventors: Chaekyu Choe, Suwon-si (KR); Hyungrock Jung, Seoul (KR); Sungmin Park, Seongnam-si (KR); Jeongje Park, Hwaseong-si (KR); Cheolho Cheong, Seoul (KR); Jaewoong Chun, Suwon-si (KR); Wonsuk Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 165 days.

(21) Appl. No.: 15/192,952

(22) Filed: Jun. 24, 2016

(65) Prior Publication Data
US 2016/0378965 A1    Dec. 29, 2016

(30) Foreign Application Priority Data

Jun. 26, 2015    (KR) ......................... 10-2015-0091566

(51) Int. Cl.
*G06F 21/32*    (2013.01)
*A61B 5/0245*    (2006.01)
(Continued)

(52) U.S. Cl.
CPC ............ *G06F 21/32* (2013.01); *A61B 5/0245* (2013.01); *A61B 5/0404* (2013.01);
(Continued)

(58) Field of Classification Search
CPC ........ G06F 21/32; G06F 3/011; G06F 21/629; G06F 1/1684; G06F 1/1626; G06F 3/015; G06F 1/1656; G06F 2203/011; A61B 5/117; A61B 5/165; A61B 2/0456; A61B 5/04; A61B 5/0245; A61B 5/0404;
(Continued)

(56) References Cited

U.S. PATENT DOCUMENTS 6,470,893 B1    10/2002   Boesen
2011/0080293 A1*   4/2011   Tanishima ............. G16H 40/63
340/573.1

(Continued)

FOREIGN PATENT DOCUMENTS

JP   2014-513628   6/2014
KR   10-2006-0129582   12/2006
KR   10-2013-0055730   5/2013

*Primary Examiner* — Matthew Smithers

(57) ABSTRACT

According to various embodiments of the present disclosure, an electronic device may include a biometric sensor configured to detect a contact signal from at least two biometric electrodes and a processor configured to determine whether the contact signal received from the biometric sensor has biological characteristics. When the processor determines that the contact signal is a biometric input having biological characteristics, the processor executes a biometric information function. When the processor determines that the contact signal does not include the biological characteristics, the processor executes a general function related to an application.

17 Claims, 23 Drawing Sheets

(51) Int. Cl.
*G06F 3/01* (2006.01)
*G06K 9/00* (2006.01)
*H04N 5/232* (2006.01)
*A61B 5/0404* (2006.01)
*A61B 5/0456* (2006.01)
*A61B 5/117* (2016.01)
*A61B 5/16* (2006.01)
*G06F 1/16* (2006.01)

(52) U.S. Cl.
CPC ............ *A61B 5/0456* (2013.01); *A61B 5/117* (2013.01); *A61B 5/165* (2013.01); *G06F 1/1626* (2013.01); *G06F 1/1656* (2013.01); *G06F 1/1684* (2013.01); *G06F 3/011* (2013.01); *G06F 3/015* (2013.01); *G06K 9/00892* (2013.01); *H04N 5/232* (2013.01); *H04N 5/23216* (2013.01); *H04N 5/23219* (2013.01); *H04N 5/23245* (2013.01); *G06F 2203/011* (2013.01); *G06K 2009/00939* (2013.01)

(58) Field of Classification Search
CPC ............. A61B 5/0456; G06K 9/00892; G06K 9/00288; G06K 2009/00939; H04N 5/23216; H04N 5/232; H04N 5/23219; H04N 5/23245
See application file for complete search history.

(56) References Cited

U.S. PATENT DOCUMENTS

| | | | |
|---|---|---|---|
| 2012/0109688 A1* | 5/2012 | Yoo .................... | G06F 19/3418 705/3 |
| 2012/0295589 A1 | 11/2012 | Alexander et al. | |
| 2013/0096649 A1* | 4/2013 | Martin ................ | G06F 19/3418 607/60 |
| 2013/0158367 A1* | 6/2013 | Pacione ............... | A61B 5/0022 600/301 |
| 2014/0081118 A1* | 3/2014 | Reinhold, Jr. ....... | A61B 5/0404 600/384 |
| 2015/0182130 A1* | 7/2015 | Utter, II ............... | A61B 5/0205 600/483 |
| 2015/0320588 A1* | 11/2015 | Connor ................ | A61F 7/0097 607/107 |
| 2016/0287177 A1* | 10/2016 | Huppert .............. | A61B 5/6833 |
| 2016/0374578 A1* | 12/2016 | Kacelenga .......... | A61B 5/0404 600/483 |
| 2017/0007180 A1* | 1/2017 | Kim .................... | A61B 5/6801 |
| 2017/0020399 A1* | 1/2017 | Shemesh ............. | A61B 5/0205 |
| 2017/0261365 A1* | 9/2017 | Kovacs ................ | G01G 19/44 |

* cited by examiner

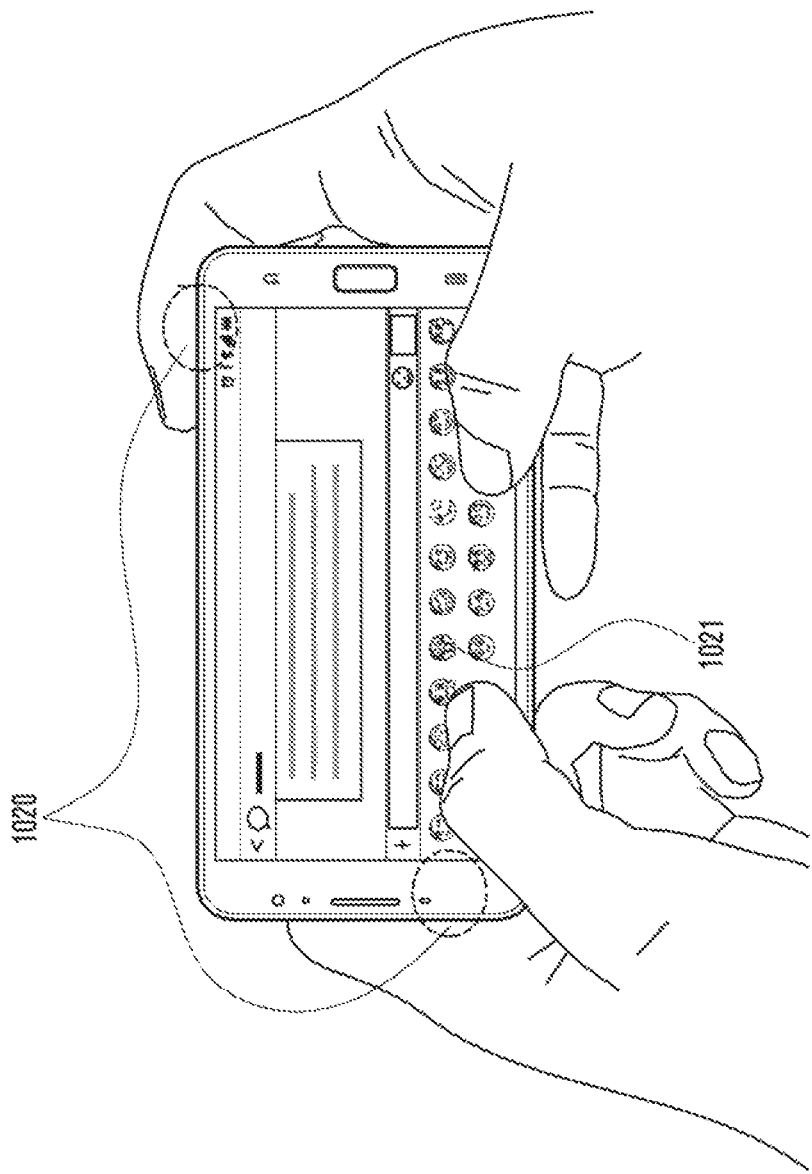

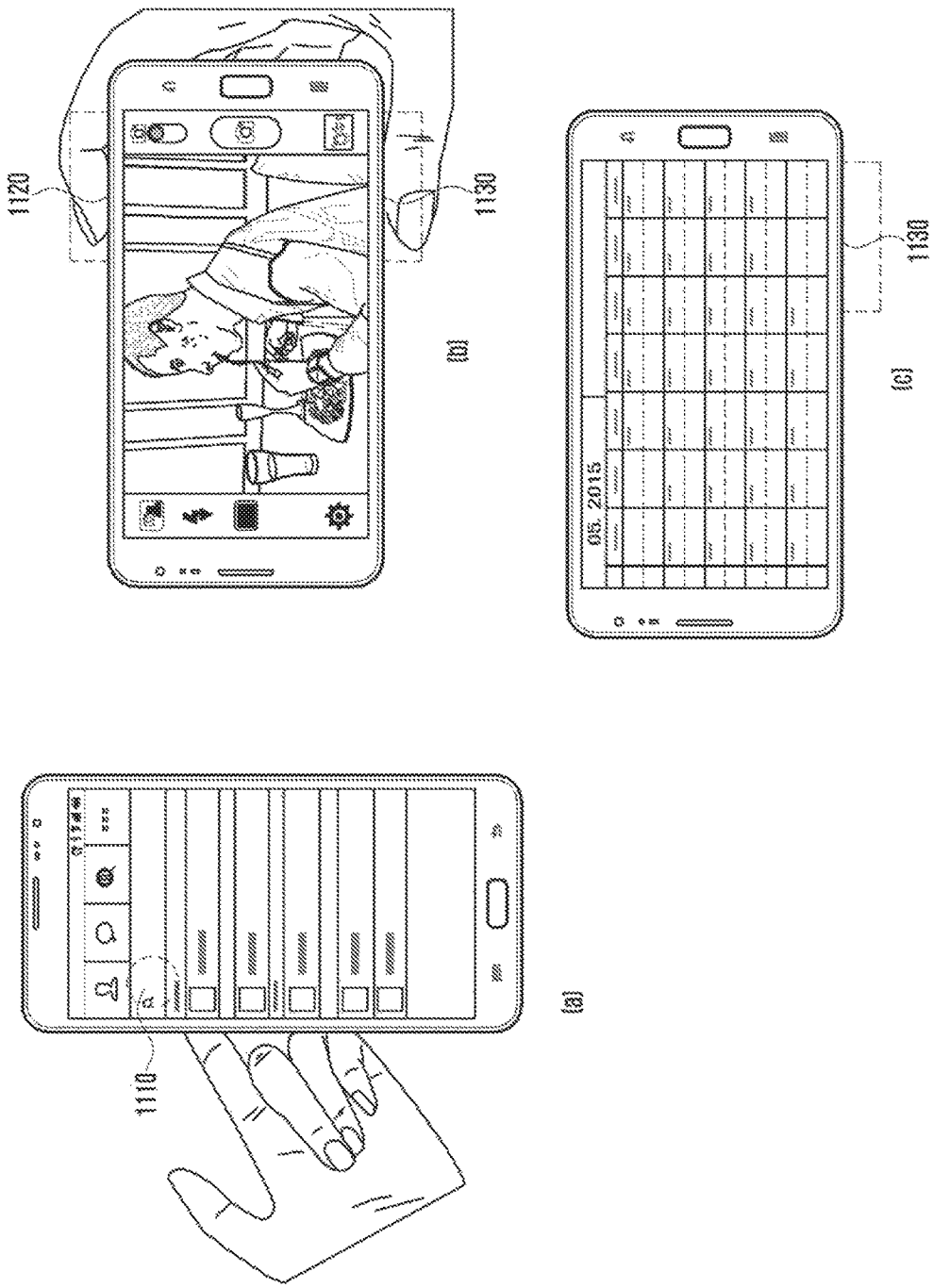

ELECTRONIC APPARATUS AND METHOD FOR CONTROLLING FUNCTIONS IN THE ELECTRONIC APPARATUS USING A BIO-METRIC SENSOR

CROSS-REFERENCE TO RELATED APPLICATION(S) AND CLAIM OF PRIORITY

The present application is related to and claims benefit under 35 U.S.C. § 119(a) of Korean Patent Application No. 10-2015-0091566, filed on Jun. 26, 2015, which is hereby incorporated by reference for all purposes as if fully set forth herein.

TECHNICAL FIELD

The present disclosure relates to an electronic apparatus and method for controlling functions in the electronic apparatus using one or more biometric sensors.

BACKGROUND

Electronic devices support complex operations of various functions thanks to the development of a hardware technology and a software technology. In recent years, as social awareness of health expands, demand for measuring and managing health states of people have increased. In response thereto, a market for providing health-related services together with an electronic device having various biometric sensors mounted thereon for measuring the health state of a user of the electronic device is forming. The biometric sensors may include a blood glucose meter, a blood pressure meter, a thermometer, a heart rate monitor (HRM), an electrocardiogram (ECG) sensor, a photo plethysmography (PPG) sensor, a fingerprint recognition device, an iris recognition device, and the like.

SUMMARY

In particular, the ECG sensor may detect, through an ECG electrode contacting a body skin, a potential difference generated when heart muscles expand and contract. An action potential generated according to heart beats causes a current which spreads from the heart throughout the entire body, and such a current generates a potential difference according to the state of the body. The ECG sensor is being used to identify the size of the heart of a user and a damage to the heart by measuring the ratio and the consistency of heart beats by detecting the electric activity of the heart. Further, the ECG sensor is variously utilized for recognizing emotional information of a user or performing user authentication using a unique ECG value as well as measuring an ECG.

However, in order to measure the ECG, ECG electrodes are attached to both arms or in different positions such as an arm or a leg, respectively, so as to form a closed loop state between the ECG measuring apparatus and the body, making it possible to acquire a meaningful ECG value from signals of the ECG electrodes. In contrast, when the closed loop state between the ECG measuring apparatus and the body is not formed, signals of the ECG electrodes are recognized as noise or as immeasurable, and thus, become biologically meaningless values. Therefore, the signals of the ECG electrodes cannot be utilized. In this way, the ECG sensor utilizes a meaningful ECG value as biometric information, and is thus limited to biometric measurement (e.g., ECG measurement, emotion measurement, user authentication, etc.).

Accordingly, various embodiments of the present invention present a method and apparatus which can utilize contact signals of a sensor electrode as various input signals without limiting a usable range of biometric sensors, e.g., an ECG sensor to measuring biometric information.

Various embodiments of the present disclosure present a method and apparatus which can utilize a biometric sensor to control an electronic device in fields other than measurement of biometric signal.

In accordance with an aspect of the present disclosure, an electronic device using a biometric electrode is disclosed. The apparatus includes: a biometric sensor configured to detect a contact signal from at least one biometric electrode, and a processor configured to determine whether the contact signal received from the biometric sensor has biological characteristics, determine that the contact signal is a biometric input when the contact signal includes the biological characteristics, so as to execute a biometric information function, and determine that the contact signal is an electrode input, so as to execute a general function related to an application when the contact signal does not include the biological characteristics.

In accordance with an aspect of the present disclosure, a method of controlling a function of an electronic device is disclosed. The method includes: detecting a contact signal from at least one biometric electrode, determining whether the contact signal of the at least one biometric electrode has biological characteristics, when the contact signal includes the biological characteristics, executing a biometric information function in response to a biometric input based on the contact signal; and when the contact signal does not includes the biological characteristics, executing a general function related to an application in response to an electrode input based on the contact signal. According to various embodiments of the present disclosure, at least one signal of a biometric sensor or a combination signal thereof is utilized for a control device of an electronic device, so as to control another function in addition to a biometric function, thereby increasing utilization of the biometric sensor, and improving convenience for a user of the electronic device.

According to various embodiments of the present disclosure, signals from electrodes of the biometric sensor, which cannot generate biometric information, are recognized as a general command input, thereby achieving a convenient control of an activation triggering function of an application and a detailed function of the application.

According to various embodiments of the present disclosure, when biometric information is generated by the electrodes of the biometric sensor, execution or change of an application function related to the biometric information can be conveniently controlled by automatically analyzing the emotional information by reciting the biometric information, or by performing user authentication.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 10A to 10D illustrate examples of function control of a biometric input according to an embodiment;

FIG. 11 illustrates an example of function control of an electrode input according to various embodiments;

DETAILED DESCRIPTION

Figure 1:
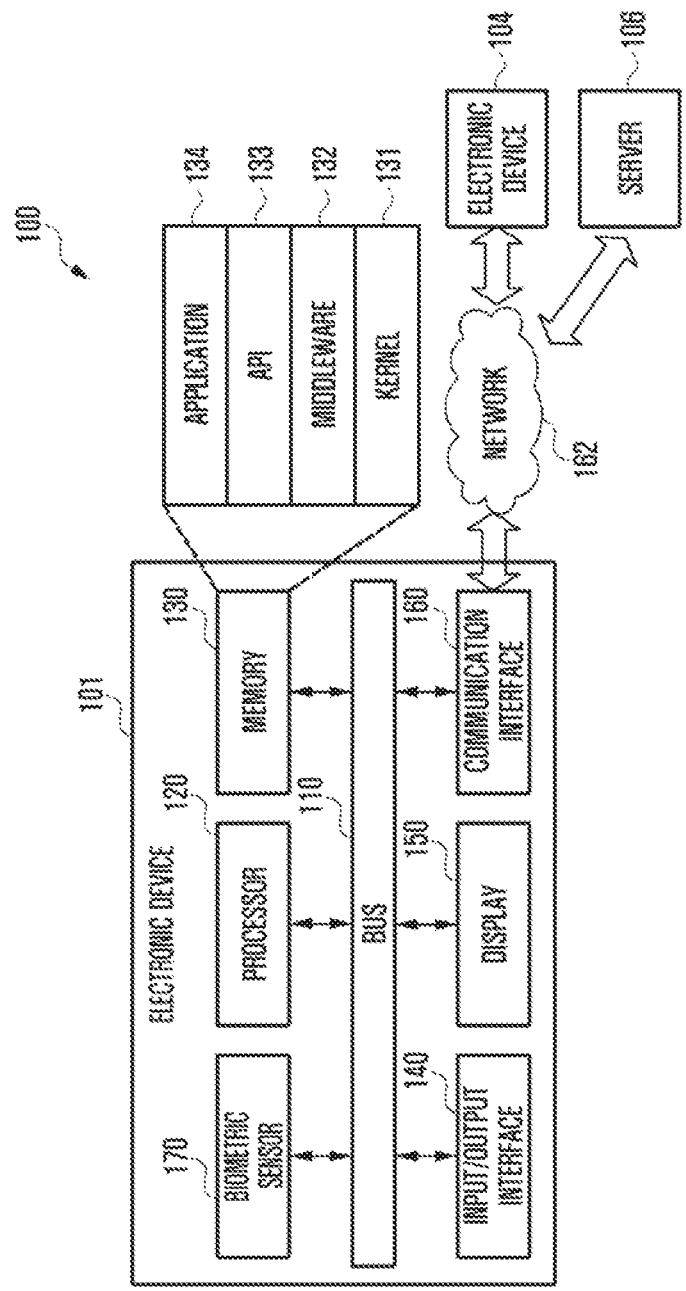
FIG. 1 is a block diagram illustrating a network environment including an electronic device according to various embodiments of the present disclosure.

FIGS. 1 through 20, discussed below, and the various embodiments used to describe the principles of the present disclosure in this patent document are by way of illustration and should not be construed in any way to limit the scope of the disclosure. Those skilled in the art will understand that the principles of the present disclosure may be implemented in any suitably arranged electronic apparatus. Hereinafter, embodiments of the present disclosure will be described in detail with reference to the accompanying drawings. It will be easily appreciated to those skilled in the art that various modifications, additions and substitutions are possible from the embodiment of the present disclosure, and the scope of the disclosure should not be limited to the following embodiments. The embodiments of the present disclosure are provided such that those skilled in the art completely understand the disclosure. In the drawings, the same or similar elements are denoted by the same reference numerals even though they are depicted in different drawings.

The expressions such as "include" and "may include" which may be used in the present disclosure denote the presence of the disclosed functions, operations, and constituent elements and do not limit one or more additional functions, operations, and constituent elements. In the present disclosure, the terms such as "include" and/or "have" may be construed to denote a certain characteristic, number, step, operation, constituent element, component or a combination thereof, but may not be construed to exclude the existence of or a possibility of the addition of one or more other characteristics, numbers, steps, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first" and "second," etc., and/or the like, may modify various elements. However, such elements are not limited by the above expressions. For example, the above expressions do not limit the sequence and/or importance of the elements. The above expressions are used merely for the purpose of distinguishing an element from the other elements. For example, a first user device and a second user device indicate different user devices although for both of them the first user device and the second user device are user devices. For example, a first element could be termed a second element, and similarly, a second element could be also termed a first element without departing from the scope of the present disclosure.

In the case where according to which a component is referred to as being "connected" or "accessed" to other component, it should be understood that not only the component is directly connected or accessed to the other component, but also another component may exist between the component and the other component. Meanwhile, in the case where according to which a component is referred to as being "directly connected" or "directly accessed" to other component, it should be understood that there is no component therebetween.

The terms used in the present disclosure are used to describe specific various embodiments, and are not intended to limit the present disclosure. Singular forms are intended to include plural forms unless the context clearly indicates otherwise.

Unless otherwise defined, all terms including technical and/or scientific terms used herein have the same meaning as commonly understood by one of ordinary skill in the art to which the disclosure pertains. In addition, unless otherwise defined, all terms defined in generally used dictionaries may not be overly interpreted.

The electronic device according to the embodiments of the present disclosure may be a device including a biometric sensor and a communication function.

For example, the electronic device corresponds to a combination of at least one of the followings: a smartphone, a tablet personal computer (PC), a mobile phone, a video phone, an e-book reader, a desktop PC, a laptop PC, a netbook computer, a personal digital assistant (PDA), a portable multimedia player (PMP), a digital audio player (e.g., MP3 player), a mobile medical device, a camera, or a wearable device. Examples of the wearable device are a head-mounted-device (HMD) (e.g., electronic eyeglasses), electronic clothing, an electronic bracelet, an electronic necklace, an appcessory, an electronic tattoo, a smart watch, etc.

The electronic device according to the embodiments of the present disclosure may include at least one of the following: the smart home appliances are a television (TV), a digital video disk (DVD) player, an audio system, a refrigerator, an air-conditioner, a cleaning device, an oven, a microwave oven, a washing machine, an air cleaner, a set-top box, a TV box (e.g., Samsung HomeSync®, Apple TV®, or Google TV®), a game console, an electronic dictionary, an electronic key, a camcorder, an electronic album, or the like.

The electronic device according to the embodiments of the present disclosure may include at least one of the following: medical devices (e.g., magnetic resonance angiography (MRA), magnetic resonance imaging (MM), computed tomography (CT), a scanning machine, an ultrasonic scanning device, etc.), a navigation device, a global positioning system (GPS) receiver, an event data recorder (EDR), a flight data recorder (FDR), a vehicle infotainment device, an electronic equipment for ships (e.g., navigation equipment, gyrocompass, etc.), avionics, a security device, a head unit for vehicles, an industrial or home robot, an automatic teller's machine (ATM), a point of sales (POS) system, etc.

The electronic device according to the embodiments of the present disclosure may include at least one of the following: furniture or a portion of a building/structure, an electronic board, an electronic signature receiving device, a projector, various measuring instruments (e.g., a water meter, an electric meter, a gas meter and a wave meter), etc., which are equipped with a heart rate measuring function, respectively. The electronic device according to the embodiments of the present disclosure may also include a combination of the devices listed above. In addition, the electronic device according to the embodiments of the present disclosure may be a flexible device. It is obvious to those skilled in the art that the electronic device according to the embodiments of the present disclosure is not limited to the aforementioned devices.

Hereinafter, electronic devices according the embodiments of the present disclosure are described in detail with reference to the accompanying drawings. In the description, the term a 'user' may be referred to as a person or a device that uses an electronic device, e.g., an artificial intelligent electronic device.

FIG. 1 illustrates a network environment 100 including an electronic device 101 according to an embodiment of the present disclosure. Referring to FIG. 1, the electronic device 101 may include a bus 110, a processor 120, a memory 130, an input/output (I/O) interface 140, a display 150, a communication interface 160 and a biometric sensor 170.

The bus 110 may be a communication circuit that connects the components to each other and transfers data (e.g., control messages) between the components.

The processor 120 may receive instructions from the components (e.g., the memory 130, input/output interface 140, display 150, communication interface 160, biometric sensor 170, etc.) via the bus 110, decode them and perform corresponding operations or data processing according to the decoded instructions.

The memory 130 may store instructions or data transferred from/created in the processor 120 or the other components (e.g., the input/output interface 140, display 150, communication interface 160, biometric sensor 170, etc.). The memory 130 may include programming modules, e.g., a kernel 131, middleware 132, application programming interface (API) 133, application module 134, etc. Each of the programming modules may be software, firmware, hardware or a combination thereof.

The kernel 131 may control or manage system resources (e.g., the bus 110, processor 120, memory 130, etc.) used to execute operations or functions of the programming modules, e.g., the middleware 132, API 133, and application module 134. The kernel 131 may also provide an interface that may access and control/manage the components of the electronic device 101 via the middleware 132, API 133, and application module 134.

The middleware 132 may make it possible for the API 133 or application module 134 to perform data communication with the kernel 131. The middleware 132 may also perform control operations (e.g., scheduling, load balancing) for task requests transmitted from the application module 134 by methods, for example, a method for assigning the order of priority to use the system resources (e.g., the bus 110, processor 120, memory 130, etc.) of the electronic device 101 to at least one of the applications of the application module 134.

The application programming interface (API) 133 is an interface that allows the application module 134 to control functions of the kernel 131 or middleware 132. For example, the API 133 may include at least one interface or function (e.g., instruction) for file control, window control, character control, video process, etc.

In embodiments of the present disclosure, the application module 134 may include applications that are related to: short message service (SMS)/multimedia messaging service (MMS), email, calendar, alarm, health care (e.g., an application for measuring the blood sugar level, a workout application, etc.), environment information (e.g., atmospheric pressure, humidity, temperature, etc.), and so on. The application module 134 may be an application related to exchanging information between the electronic device 101 and the external electronic devices (e.g., an electronic device 104). The information exchange-related application may include a notification relay application for transmitting specific information to an external electronic device or a device management application for managing external electronic devices.

For example, the notification relay application may include a function for transmitting notification information, created by the other applications of the electronic device 101 (e.g., SMS/MMS application, email application, health care application, environment information application, etc.), to an external electronic device (e.g., electronic device 104). In addition, the notification relay application may receive notification information from an external electronic device (e.g., electronic device 104) and provide it to the user. The device management application may manage (e.g., to install, delete, or update): part of the functions of an external electronic device (e.g., electronic device 104) communicating with the electronic device 101, e.g., turning on/off the external electronic device, turning on/off part of the components of the external electronic device, adjusting the brightness (or the display resolution) of the display of the external electronic device, etc.; applications operated in the external electronic device; or services from the external electronic device, e.g., call service or messaging service, etc.

In embodiments of the present disclosure, the application module 134 may include applications designated according to attributes (e.g., type of electronic device) of the external electronic device (e.g., electronic device 104). For example, if the external electronic device is an MP3 player, the application module 134 may include an application related to music playback. If the external electronic device is a mobile medical device, the application module 134 may include an application related to health care. In an embodiment of the present disclosure, the application module 134 may include at least one of the following: an application designated in the electronic device 101 and applications transmitted from external electronic devices (e.g., server 106, electronic device 104, etc.).

The input/output interface 140 may receive instructions or data from the user via an input/output system (e.g., a sensor, keyboard or touch screen) and transfers them to the processor 120, memory 130, communication interface 160, or biometric sensor 170 through the bus 110. For example, the input/output interface 140 may provide data corresponding to a user's touch input to a touch screen to the processor 120. The input/output interface 140 may receive instructions or data from the processor 120, memory 130, communication interface 160, or biometric sensor 170 through the bus 110, and output them to an input/output system (e.g., a speaker or a display). For example, the input/output interface 140 may output voice data processed by the processor 120 to the speaker.

The display 150 may display information (e.g., multimedia data, text data, etc.) on the screen so that the user may view it.

The communication interface 160 may communicate between the electronic device 101 and an external system (e.g., an electronic device 104 or server 106). For example, the communication interface 160 may connect to a network 162 in wireless or wired mode and communicate with the external system. Wireless communication may include at least one of the following: Wi-Fi®, Bluetooth® (BT), near field communication (NFC), global positioning system (GPS) or cellular communication (e.g., LTE, LTE-A, CDMA, WCDMA, UMTS, Wi-Bro, GSM, etc.). Wired communication may include at least one of the following: universal serial bus (USB), high definition multimedia interface (HDMI), recommended standard 232 (RS-232), plain old telephone service (POTS), etc.

In an embodiment of the present disclosure, the network 162 may be a telecommunication network. The telecommunication network may include at least one of the following: a computer network, Internet, Internet of things, telephone network, etc. The protocol for communication between the electronic device 101 and the external system, e.g., transport layer protocol, data link layer protocol, or physical layer protocol, may be supported by at least one of the following: application module 134, API 133, middleware 132, kernel 131 and communication module 160 The biometric sensor 170 may be a biometric sensor including at least one electrode. The biometric sensor 170 may include a sensor, e.g., an HRM, an ECG sensor, a PPG sensor, and the like, which can receive an electrical change of a body by making contact with the body through the electrode.

The processor 120 can process a signal or data transmitted from the biometric sensor 170 and control biometric information analysis, a user function of the electronic device, and an operation of the application on the basis of the processed signal or data. The processor 120 can determine whether a contact signal received from each electrode of the biometric sensor 170 is a biometric input or an electrode input, control a biometric information function or an application associated with biometric information when it is determined that the contact signal is the biometric input, and control a general function (e.g., an application operation) separate from the biometric information when it is determined that the contact signal is the electrode input.

Additional information on a function of the processor 120 is provided through FIG. 2 described below.

Figure 2:
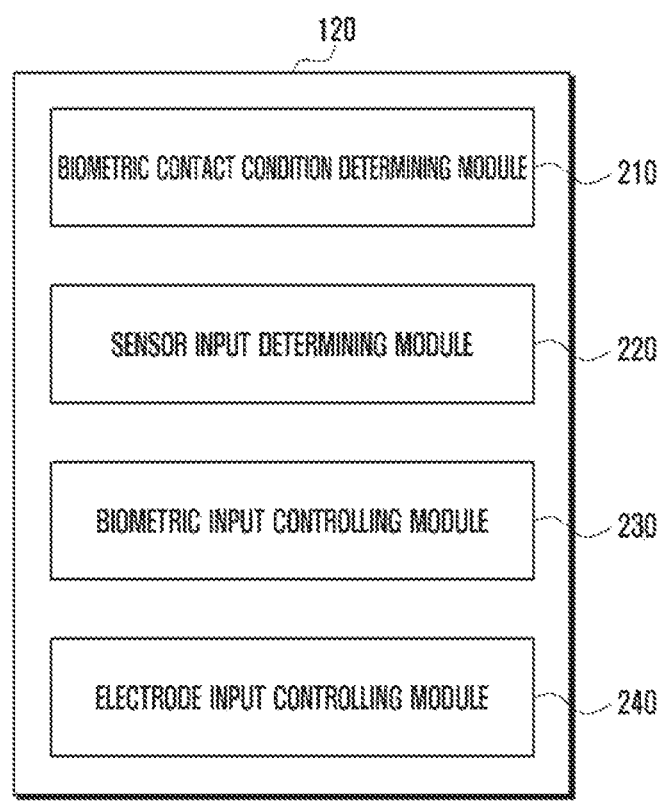
FIG. 2 is a block diagram illustrating a configuration of an electronic device according to various embodiments of the present disclosure.

FIG. 2 is a block diagram illustrating a configuration of a processor of an electronic device according to various embodiments.

Referring to FIG. 2, the processor 120 may include a biometric contact condition determining module 210, a sensor input determining module 220, a biometric input controlling module 230, and an electrode input controlling module 240. Hereinafter, for convenience of description, it will be described that the biometric sensor 170 is an ECG sensor including at least two electrodes. However, the present disclosure is not limited thereto. The ECG sensor can detect a biometric potential signal detected between each of electrodes, and can measure (or record) an ECG of a user by amplifying the same.

The biometric contact condition determining module 210 can determine whether a body (or an electrical conductor) is in contact therewith, using a change in voltage changed according to a contact state of each electrode. The biometric contact condition determining module 210 can determine a contact detection condition on the basis of at least one of a position of an electrode where a contact signal is generated from among the electrodes of the biometric sensor, a contact maintaining time of the electrode, the number of contact electrodes, and a contact and detachment state of the electrode.

Figure 3:
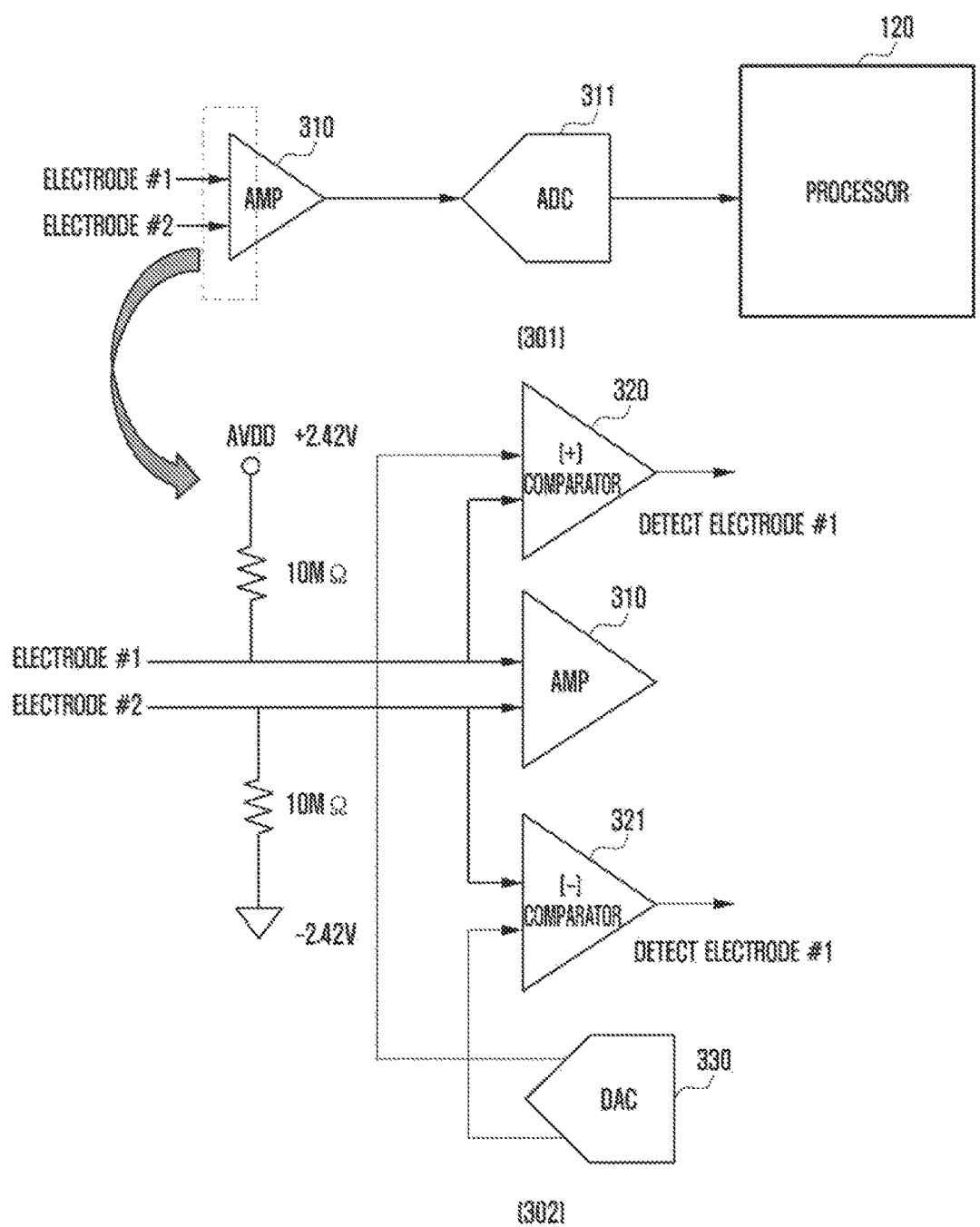
FIG. 3 illustrates an example of a circuit diagram of an ECG sensor electrode according to various embodiments of the present disclosure.

According to an embodiment, FIG. 3 illustrates an example where a circuit diagram of an ECG sensor is implemented. As illustrated in reference numeral 301, when the body of a user contacts at least two electrodes (e.g., an electrode #1 and an electrode #2) configured in the electronic device, a biometric contact signal is transmitted to an analog-digital converter (ADC) through a signal amplifier 310, and data transformed into a digital signal by the ADC 311 is transmitted to the processor 120. When an ECG sensor is expanded, as illustrated in reference numeral 302, the at least two electrodes (e.g., the electrode #1, and the electrode #2) constituting the ECG sensor can be connected to comparators 320 and 321 and an analog voltage terminal (AVDD). For example, when the body of the user comes into contact with the electrodes (e.g., the electrode #1 and the electrode #2), voltage of a power source (e.g., ±2.42V) applied through the AVDD by an action potential difference of the body transmitted from each electrode is changed, and a signal having the changed voltage is compared with a signal of the DAC 330 through the Comparators 320 and 321, so as to detect contact with a body.

The biometric contact condition determining module 210 can identify occurrence of a contact with each electrode and a position of an electrode contacting the body, measure a time when a voltage change occurs through the voltage change (e.g., comparison between 8 types of voltage changes by a 3-bit DAC) obtained by using one or more of the DAC 330 (e.g., a 4-bit DAC), the (+) comparator 320, and the (−) comparator 321, and identify a body attachment/detachment state through a state change of a voltage change signal.

When there is no voltage change of a signal output through the comparators or the voltage change is not within a predetermined range, the biometric contact condition determining module 210 may determine that a current state is a non-contact state in which an electrode is not in contact with the body (or conductor).

According to an embodiment, the biometric contact condition determining module 210 may determine whether an object contacting the electrode of the biometric sensor is a living body or a non-living body. For example, the biometric contact condition determining module 210 can determine that there is contact with a living body when a voltage change occurs in a signal generated due to an object contacting an electrode within a predetermined range (e.g.: ADVO—300 mV) and determine that there is contact with a non-living body when the voltage change deviates from the predetermined range.

The sensor input determining module 220 can determine whether a biometric contact signal can generate biometric characteristics or biometric information.

For example, the sensor input determining module 220 can determine that the biometric contact signal is a signal having biometric characteristics when the biometric contact signal can be classified into P, Q, R, S and T waves, which are basic waveforms, or an interval between R waves, the number of heart beats, and the like are within a measurement range of a biometric signal of a human, or when a value of voltage, resistance, or capacitance detected through the electrode are within a predetermined range or a change value within the predetermined range. As another example, the sensor input determining module 220 can extract an R wave, and then determine a specific element of each wave using one or more of a QRS width and an ST slope, so as to determine whether the biometric contact signal is a signal having biometric characteristics.

The sensor input determining module 220 can determine that the biometric contact signal is a biometric input when the biometric contact signal has biological characteristics or it is possible to generate the biometric information, and determine that the biometric contact signal is an electrode input when the biometric contact signal does not have biometric characteristics or it is impossible to generate the biometric information. Here, the biometric input implies an input generating a function command related to the biometric information when the contact signal of the electrode has biometric characteristics and it is possible to generate the biometric information. The electrode input implies an input generating a function command related to an application when it is impossible to measure the ECG, recognize the biometric information, and generate the emotional information because the contact signal of the electrode cannot generate the biometric information.

The sensor input determining module 220 can determine an operation state of the electronic device on the basis of at least one of a locking state of the electronic device, an application driving state of the electronic device, the type of a driven application, and a holding state of the electronic device. The sensor input determining module 220 can identify a body contact detecting condition and an operation state of the electronic device and generate a command corresponding to a command or an electrode command corresponding to the biometric input. The command corresponding to the command or the electrode command corresponding to the biometric input can be preconfigured for each body contact condition and each operation state of the electronic device.

For example, a command for performing a user authentication executing operation in response to the biometric input of the locking state of the electronic device and performing an unlocking operation when authentication is successfully completed is configured (or generated), a messenger application function can be changed or a command for providing emotional state information can be configured (or generated) in reflection of an emotional state by identifying a user emotional state on the basis of the biometric information to correspond to the biometric input of an application execution state. As another example, a command for performing a first operation of an application or a command for performing a second operation of the application can be configured (or generated) for each contact position of the electrode input and for each condition to correspond to the electrode input of the application execution state.

The biometric input controlling module 230 can make a control to automatically operate an application (e.g., a health management application, and the like) related to the biometric information in response to the biometric input based on the body contact signal.

The biometric input controlling module 230 can analyze the biometric information in response to the body contact signal or control an application function related to the biometric information on the basis of the biometric characteristics, in response to the biometric input based on the body contact signal.

When the body contact signal is a biometric input, the biometric input controlling module 230 can analyze the biometric information so as to analyze an emotional state of a user and generate emotional information. As an example, the biometric input controlling module 230 can analyze the number of heart beats or a heart rate variability (HRV) by measuring the number of R-wave signals among body contact signals (e.g., an ECG signal). The biometric input controlling module 230 can analyze an activity of an autonomic nerve (e.g., stress information related to a sympathetic nerve and a parasympathetic nerve, etc.) by detecting a change between heart beats by measuring a change in a time interval R-R between R waves (peaks), and identify an emotional state of a user on the basis of characteristics of the activity. The biometric input controlling module 230 can determine or detect prediction information on an irregular pulse, a heart attack, and the like, through an HRV analysis. The biometric input controlling module 230 may, in order to measure an interval between heart beats, calculate a difference between occurrence times by receiving an event signal at every peak or measure an R-R interval by continuously collecting the number of heart beats generated during a predetermined time period.

The biometric input controlling module 230 can generate emotional information according to an emotional state (e.g., happy, sad, surprise, awakening, angry, or the like) of a user by analyzing an HRV, and determine a level (e.g., an emotion step/emotion peak step or a peak-to-ratio) corresponding to the emotional state of the user through an HRV value.

When the emotional information of the user is generated based on the biometric characteristics, the biometric input controlling module 230 can make a control to execute a function based on the emotional information or change a function of the application according to the emotional information while interworking with an application being running. For example, when emotional information is generated in a camera operation state, the biometric input controlling module 230 can perform a function of tagging the emotional information measured on a shooting image. When emotional information is generated in a message writing state, the biometric input controlling module 230 can make a control to transmit the emotional information together with a written message to a counterpart electronic device. When emotional information is generated during a call connection with a counterpart, the biometric input controlling module 230 can control a function of changing the background of the electronic device according to the emotional information.

The biometric input controlling module 230 can perform user authentication on the basis of characteristics of the biometric information (e.g., an ECG wave) of the user in response to the biometric input based on the contact signal. For example, the ECG wave of the biometric signal of the user reflects features related to a position and a shape of the heart of the user. The biometric input controlling module 230 can calculate the similarity between an ECG waveform acquired by the body contact signal and biometric characteristics (e.g., the rhythm and the pattern of the ECG waveform, the peak of the waveform, and the slope characteristic information) of a user pre-stored in the electronic device, and determine that the user authentication is successfully completed when the similarity corresponds to a predetermined criterion (e.g., the matching degree of 90% of higher).

The biometric input controlling module 230 can make a control to automatically perform an operation related to authentication through the ECG measurement in response to the biometric input when the authentication is required through the electronic device or an application requiring the authentication is driven.

The biometric input controlling module 230 can make a control to allow or change the right of a function of the electronic device/a function of the application on the basis of the user authentication using the biometric information. For example, the biometric input controlling module 230 can make a control to execute a function permitted according to the right of a user when the user authentication is successfully completed and restrain the function of the electronic device/the function of the application when the user authentication fails.

For example, the biometric input controlling module 230 can make a control to change health information or recommendation information provided to the user in real-time, when the user authentication is successfully completed while a health management application is executed. The biometric input controlling module 230 can make a control to not change the health information or the recommendation information provided to the user when the user authentication fails. As another example, the biometric input controlling module 230 can store the authentication-failed biometric information in a server or the electronic device, and provide information related thereto (e.g., authentication-failed related information and ECG related information) and authentication failure notification information through a rightful account, and the like (e.g., an e-mail, an SNS, and an MMS) of the user.

The electrode input controlling module 240 can control an operation (e.g., application triggering, and a detailed function of a specific application) of the application in response to the electrode input which cannot generate the biometric information on the basis of the body contact signal. Here, the electrode input may be command information having a shape such as a key input signal using a signal of the ECG electrode.

The electrode input controlling module 240 can trigger activation of an application mapped to each detection condition of the body contact signal to correspond to the electrode input based on the body contact signal.

The electrode input controlling module 240 can make a control to execute a function of an application being running mapped to each detection condition of the body contact signal to correspond to the electrode input based on the body contact signal, in an application running state. For example, in a state in which a camera is executed, the electrode input controlling module 240 can make a control to perform a function control (e.g., one or more of shooting, selecting of a camera menu, focusing zoom, and timer shooting) of the camera to correspond to the electrode input.

FIGS. 4A to 4H illustrate examples of an ECG sensor electrode according to various embodiments of the present disclosure.

Referring to FIGS. 4A to 4H, ECG electrodes of an ECG sensor are exposed to the outside of the electronic device so as to be in direct contact with the body. For example, the ECG electrodes may be arranged in various positions of the electronic device among the front surface, the bezel, the side, the corner, and the input key (button) of the electronic device.

In another embodiment, the ECG electrodes may be mounted to an external electronic device (e.g., a wearable device and portable medical equipment) connected to the electronic device. In this case, the external electronic device can transmit an electrical change of the body, measured by the ECG electrodes mounted to the external electronic device, to the electronic device.

In another embodiment, the ECG sensor (or the ECG electrodes) may be mounted to a case of the electronic device. In this case, the electronic device can acquire an electrical change of the body, measured by the ECG electrodes mounted to the case, through a connection part of the electronic device making contact with the case.

The ECG electrodes may be a part of a conductor having a shape of a metal bezel or a metal button or may be functionally connected to the metal bezel or the metal button.

The ECG electrodes may be arranged in the electronic device while being separated from each other in order to prevent short-circuiting and shorting. For example, one ECG electrode (or a conductor connected to the ECG electrode) may be arranged to be spatially separated from another adjacent ECG electrode (or a conductor connected thereto) or so as not to be in contact with another adjacent ECG electrode through a nonconductive material (e.g., plastic). Otherwise, a material having different conductivity may be arranged between the one ECG electrode and another ECG electrode. For example, when each ECG electrode is arranged on a metal bezel or a metal side, each ECG electrode may be a silver mixture, and the bezel part may be a metal or aluminum having relatively low conductivity. At this time, when the ECG electrodes are arranged to be spaced apart from each other by a constant interval, a resistance value between the ECG electrodes is increased, short-circuiting and shorting may not occur between the ECG electrodes.

FIGS. 4A to 4H illustrate various embodiments for an arrangement configuration of the ECG electrodes. The ECG sensor may include at least two electrodes, and the ECG electrodes may be arranged in various positions such as the front surface, the bezel, the side, the corner, the input key (e.g., a button part), and the like of the electronic device.

In FIGS. 4A to 4H, although the ECG electrodes are illustrated for a left electrode L, a right electrode R, and a ground electrode G, an arrangement position of each ECG electrode may be changed. Here, a contact portion between the ground G electrode and the body may be not limited.

Figure 4D:
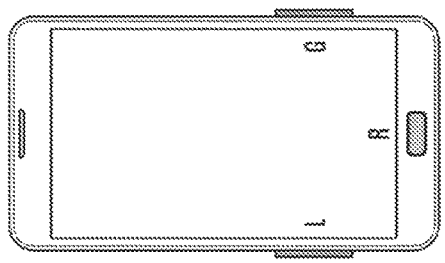
FIGS. 4A to 4H illustrates various examples of an ECG sensor electrode placement according to various embodiments of the present disclosure.
Figure 4H:
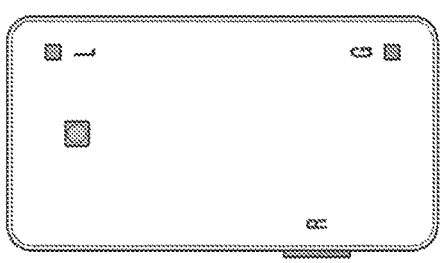
Figure 4C:
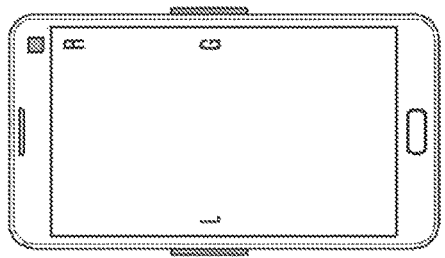
Figure 4G:
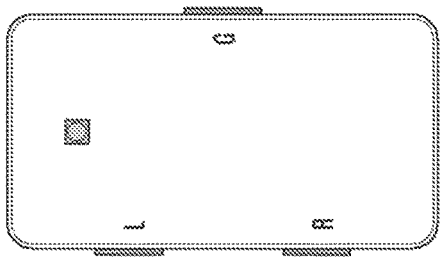
Figure 4B:
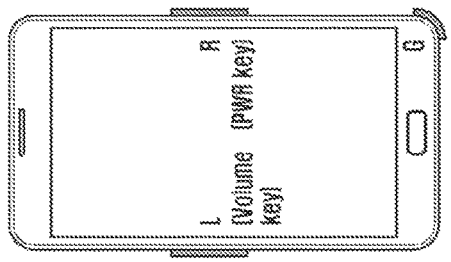
Figure 4F:
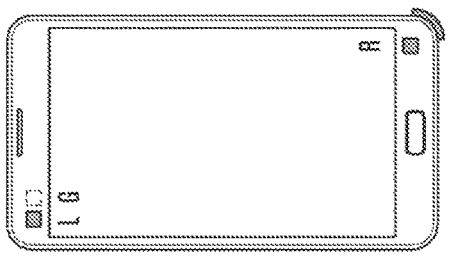
Figure 4A:
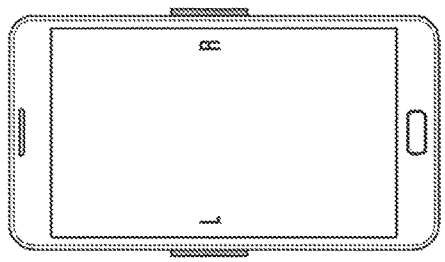

FIG. 4A is an example where the L electrode and the R electrode are arranged on both side surfaces. In this case, when one hand is in contact with the L electrode and the other hand is in contact with the R electrode, biometric information having biometric characteristics can be generated, and a contact signal can be determined as a biometric input. In contrast, when the body is in contact with only one electrode, since the biometric information having biometric characteristics cannot be generated, a body contact signal can be determined as an electrode input.

Figure 4E:
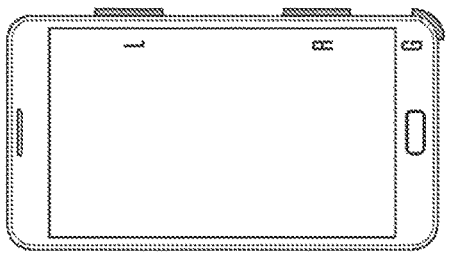

According to an embodiment, as illustrated in FIG. 4B, some of the ECG electrodes of the electronic device may be arranged inside a hardware button device such as a volume key, a power key, and a home key or mounted on the button device. In FIG. 4B, the L electrode may be coupled to the volume key, the R electrode may be arranged in a form coupled to the power key, and the G electrode may be arranged at a corner of the electronic device. FIGS. 4C and 4D illustrate examples where the ECG electrodes are arranged on the front surface of the electronic device, and FIG. 4E illustrates an example where the ECG electrodes are arranged on a side part of the electronic device.

According to an embodiment, as illustrated in FIGS. 4F and 4G, some of the ECG electrodes of the electronic device may be arranged on the front surface of the electronic device, and the other ECG electrodes may be arranged on the rear surface of the electronic device. FIG. 4H illustrates an example where the ECG electrodes are arranged on the rear surface of the electronic device.

Figure 5:
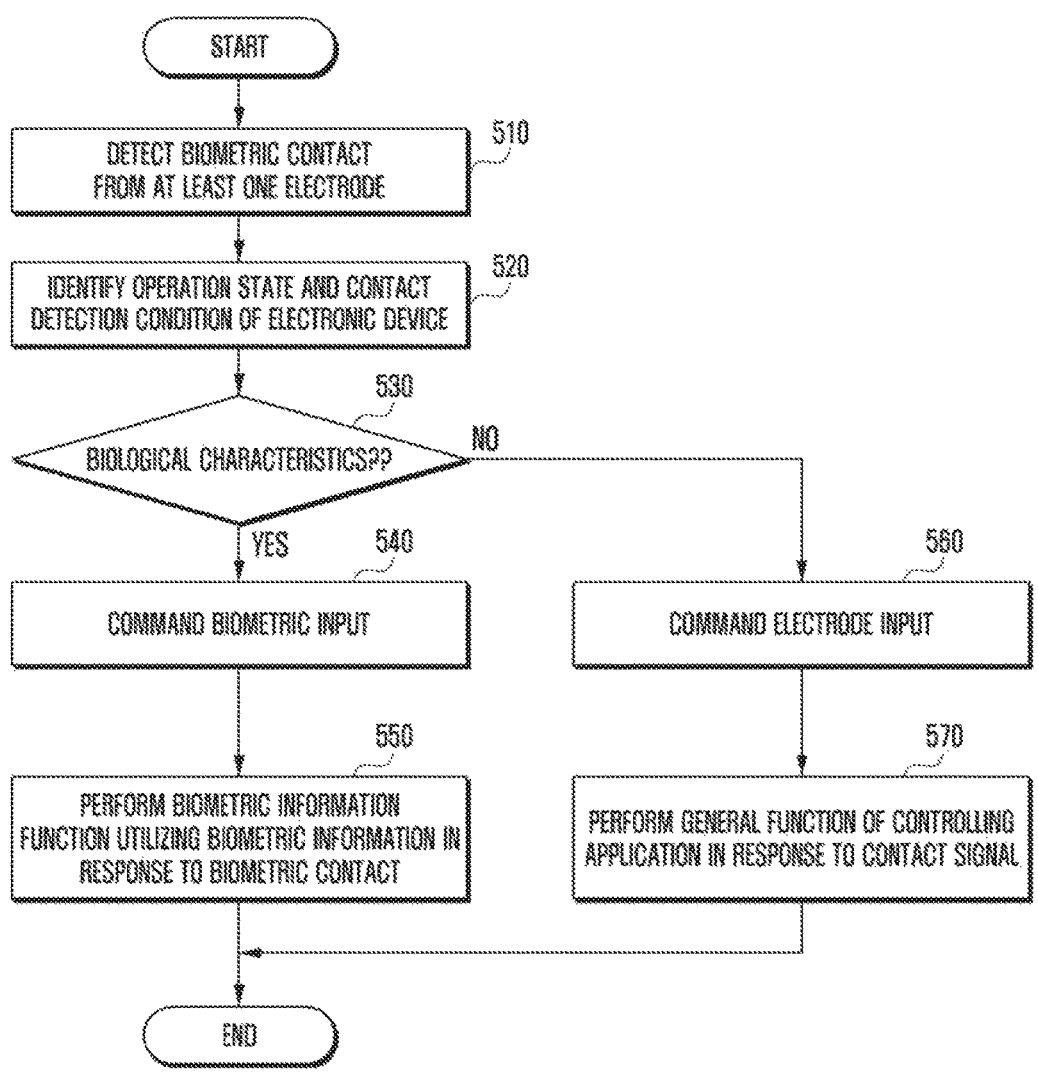
FIG. 5 illustrates a method of controlling a function using a biometric sensor according to various embodiments of the present disclosure.

FIG. 5 illustrates a method of controlling a function using a biometric sensor according to various embodiments of the present disclosure.

Referring to FIG. 5, a processor of an electronic device receives an ECG signal according to contact with a body through at least one ECG electrode or a combination thereof, in operation 510.

In operation 520, the processor identifies an operation state and a contact detection condition of the electronic device. For example, the processor can identify at least one state among a locking state, an application running state, the type of running application, and a holding state of the electronic device. The processor can identify a contact detection condition through at least one of a position of an ECG electrode contacting a body, a body contact time, a body contact and detachment state, and the number of ECG electrodes making contact with the body.

In operation 530, the processor determines whether the ECG signal includes biometric characteristics which can generate biometric information, on the basis of the ECG signal. The processor proceeds to operation 540 to determine that the ECG signal is a biometric input command when it is possible to generate biometric information (e.g., an ECG value) from the ECG signal, and proceeds to operation 560 to determine that the ECG signal is an electrode input command when it is impossible to generate the biometric information (e.g., the ECG value) from the ECG signal.

Although it is illustrated in an embodiment that operation 520 and operation 530 are sequentially performed, the present disclosure is not limited thereto. It is probable to perform operation 530 and then operation 520, or to perform operation 520 and operation 530 in parallel.

For example, when both the left side and the right side of the body of a user comes into contact with the ECG electrode or contact with a body occurs at all ECG electrodes, the processor can measure an ECG value through a voltage change generated due to contact of an ECG electrode, and thus, determine that the ECG signal includes biometric characteristics.

In operation 550, when it is determined that the ECG signal is a biometric input, the processor performs a biometric information function utilizing biometric information in response to the ECG signal.

Here, the biometric information function may be a function of utilizing biometric information (e.g., the ECG value) generated by biometric characteristics or a function of overlappingly controlling an application or applications associated with the biometric information. For example, the biometric information function may include at least one of a function of automatically executing an application utilizing the biometric information, a function of executing user authentication through the biometric information or an application related thereto, a function of measuring emotional information on the basis of biometric information and controlling a function of an application utilizing the emotional information, and a function of unlocking the electronic device through biometric authentication or executing a security function. The electronic device can control various biometric information functions according to a set condition on the basis of an operation state of the electronic device.

In an embodiment, when a biometric input based on the ECG signal is generated in a state in which the electronic device is in a locked state, the electronic device can perform user authentication on the basis of the biometric information generated from the ECG signal, and when the user authentication is successfully completed, the electronic device is unlocked (or the electronic device is unlocked and a biometric information providing application is activated).

In an embodiment, when a biometric input based on the ECG signal is generated while the electronic device executes a particular application, the electronic device can determine the emotional information of a user on the basis of the biometric information, and apply the emotional information to the application being running, so as to change a function of an application or provide a new function.

In operation 570, when it is determined that an electrode input is generated, the processor performs a general function for controlling an application to correspond to the ECG signal. Herein, since the biometric information cannot be generated on the basis of the ECG signal, the general function may be a function of controlling an application according to an operation state of the electronic device regardless of the biometric information. For example, the general function may include a function of selecting a menu on an application, a function of performing an additional input in addition to a separate input button, and a function of triggering activation of an application.

In an embodiment, when the electronic device is in an operation mode, and an electrode input based on the ECG signal is generated, the electronic device can make a control to activate an application mapped to each body contact condition of the ECG signal.

In an embodiment, when the electronic device is executing the camera application and an electrode input based on the ECG signal is generated, the electronic device can make a control to execute a function corresponding to at least one of a shooting operation, a camera menu selecting operation, a focusing-zoom operation, and a timer shooting selecting operation.

Figure 6:
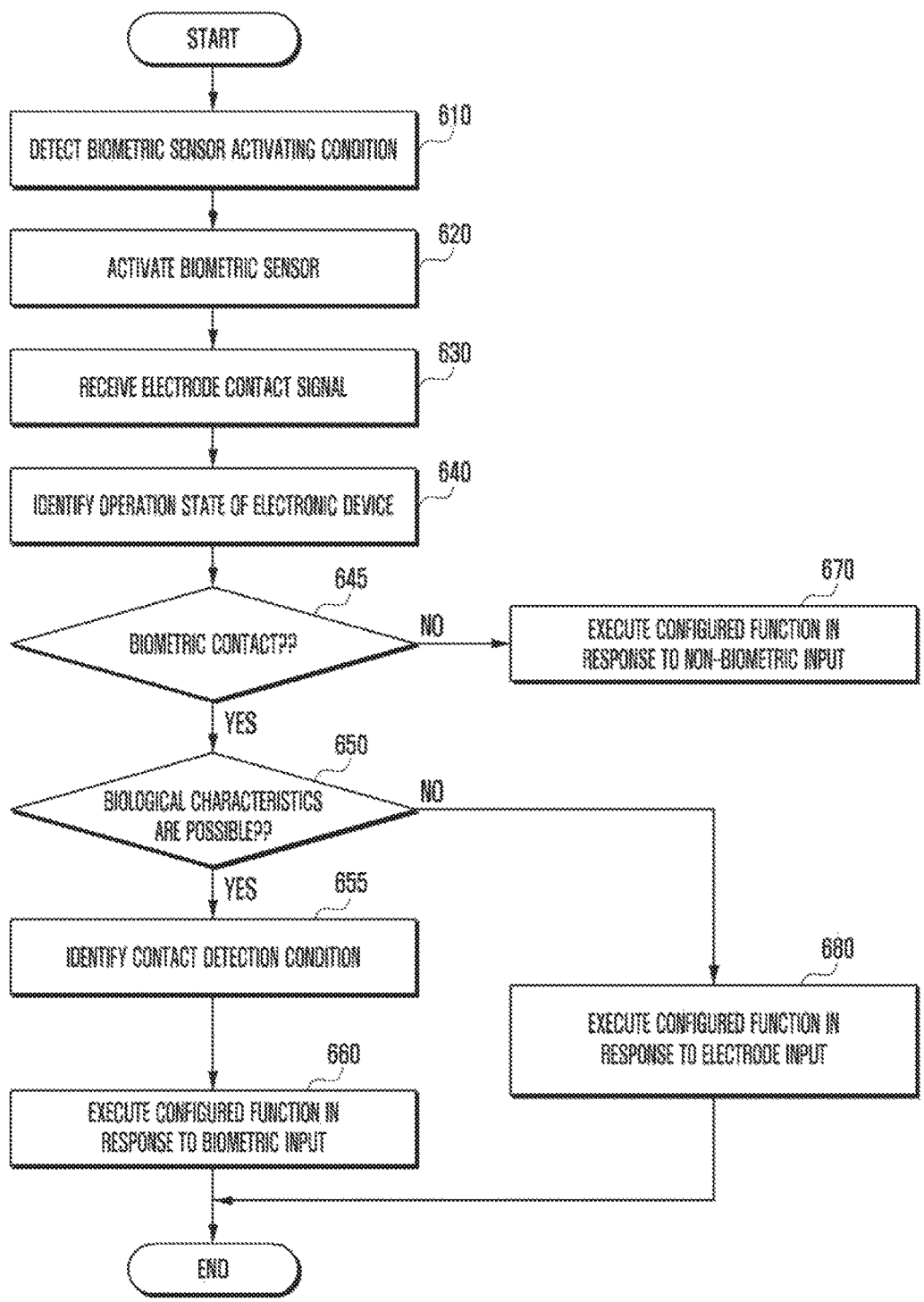
FIG. 6 illustrates a method of controlling a function of an electronic device using a biometric sensor according to various embodiments of the present disclosure.

FIG. 6 illustrates a method of controlling a function of an electronic device using a biometric sensor according to various embodiments of the present disclosure.

Referring to FIG. 6, a processor of an electronic device detects a biometric sensor activation condition, in operation 610, and activates (e.g., operates) a biometric sensor in response to the detection of the biometric sensor activation condition in operation 620. The biometric sensor activation condition may be changed according to an operation state of the electronic device. The biometric sensor activation condition may be a time point when a specific application runs or a time point when a specific set operation is performed while an application is running, the biometric sensor activation condition may be preconfigured or a setting condition thereof may be changed. As an example, the biometric sensor activation condition may include at least one of a condition in which a camera function is activated (e.g., an image sensing application or a camera related application runs), a condition in which a function of the front camera or the rear camera is operated (e.g., a camera app is operated or a preview image is received), a condition in which the face of a user of the electronic device is recognized within an image included in the preview image, a condition in which an object comes in contact with one or more of the ECG electrodes, a condition in which information on a pose or a gesture is acquired using a motion sensor of the electronic device, a condition in which a specific signal is sensed on the basis of sensors included in the electronic device, and a condition in which a request input of a user is detected.

After activating the biometric sensor, the electronic device receives an electrode contact signal in operation 630 and identifies an operation state of the electronic device in operation 640. In operation 645, the electronic device determines of the contact signal is a biometric input. If the contact signal is not a biometric input, the processor executes a configured function in response to a non-biometric input in operation 670. If the contact signal is a biometric input, in operation 650, the processor determines if biological characteristics are possible. If biological characteristics are not possible, the processor executes a configured function in response to an electrode input in operation 680. If biological characteristics are possible, the processor identifies a contact detection condition in operation 655 and executes a configured function in response to a biometric input in operation 660.

According to an embodiment, the processor can make a control to detect a biometric signal by operating the ECG sensor under a specific condition after the camera function is operated. For example, when a camera (e.g., a front camera or a self-camera) is operated and a preview image is displayed on a display, if the face of a user is recognized by analyzing an image input by the corresponding camera, the processor can make a control to operate a biometric sensor.

The processor can make a control to operate the biometric sensor in response to a condition in which an object (e.g., a finger) comes into contact with one or more of the ECG electrodes.

The processor can determine an operating condition of the biometric sensor on the basis of information on a pose or a gesture (e.g., information on movement or a pitch, a yaw, and a roll on a three-dimensional space) using the motion sensor of the electronic device. For example, the electronic device is placed on a table or the bottom, the camera or the biometric sensor to be operated may face the ground. The processor can make a control to detect a pose of the electronic device through an accelerometer or a gyro sensor, and so as not to operate the ECG sensor when at least one condition is satisfied if it is determined that the camera or the biometric sensor to be used for shooting is located horizontal to or close to the ground or the size of a movement signal is equal to or lower than a configured value. In contrast, the processor can make a control to operate the biometric sensor when the at least one condition is satisfied if, as a result of analyzing a pose signal of the electronic device, the camera or the biometric sensor is not closely horizontal to the ground or the size of the movement signal is equal to or higher than a configured value.

According to various embodiments, the processor can sequentially determine the biometric sensor activation condition by a priority when a plurality of conditions is simultaneously satisfied in order to operate the biometric sensor.

According to an embodiment, when the ECG sensor is not activated, the processor can make a control to automatically activate the ECG sensor when a switch is made to the front camera.

According to an embodiment, when a touch input is detected on a specific location of the preview image in the camera operation state, the processor can make a control to operate the biometric sensor. Otherwise, the processor can make a control to operate the biometric sensor when a user input is detected through a hardware button or a touch sensor mounted to a size, a bezel, or a housing of the rear part of the electronic device in the camera operation state.

According to various embodiments, when a processor (e.g., an Application Processor (AP)) is in a sleep mode or is powered off, if a user input is detected on a hardware button or a touch region (e.g., a power on/off function or a home key button) having an ECG electrode embedded or mounted therein, the processor can make a control to operate in an active state in response to the user input, and make a control to apply power to the biometric sensor in response thereto, or operate the biometric sensor.

Hereinafter, an example of function control corresponding to the biometric input and the electrode input will be described. The example is merely exemplified for the detailed description of the disclosure, and the present disclosure is not limited thereto.

Biometric Input Embodiment

Figure 7:
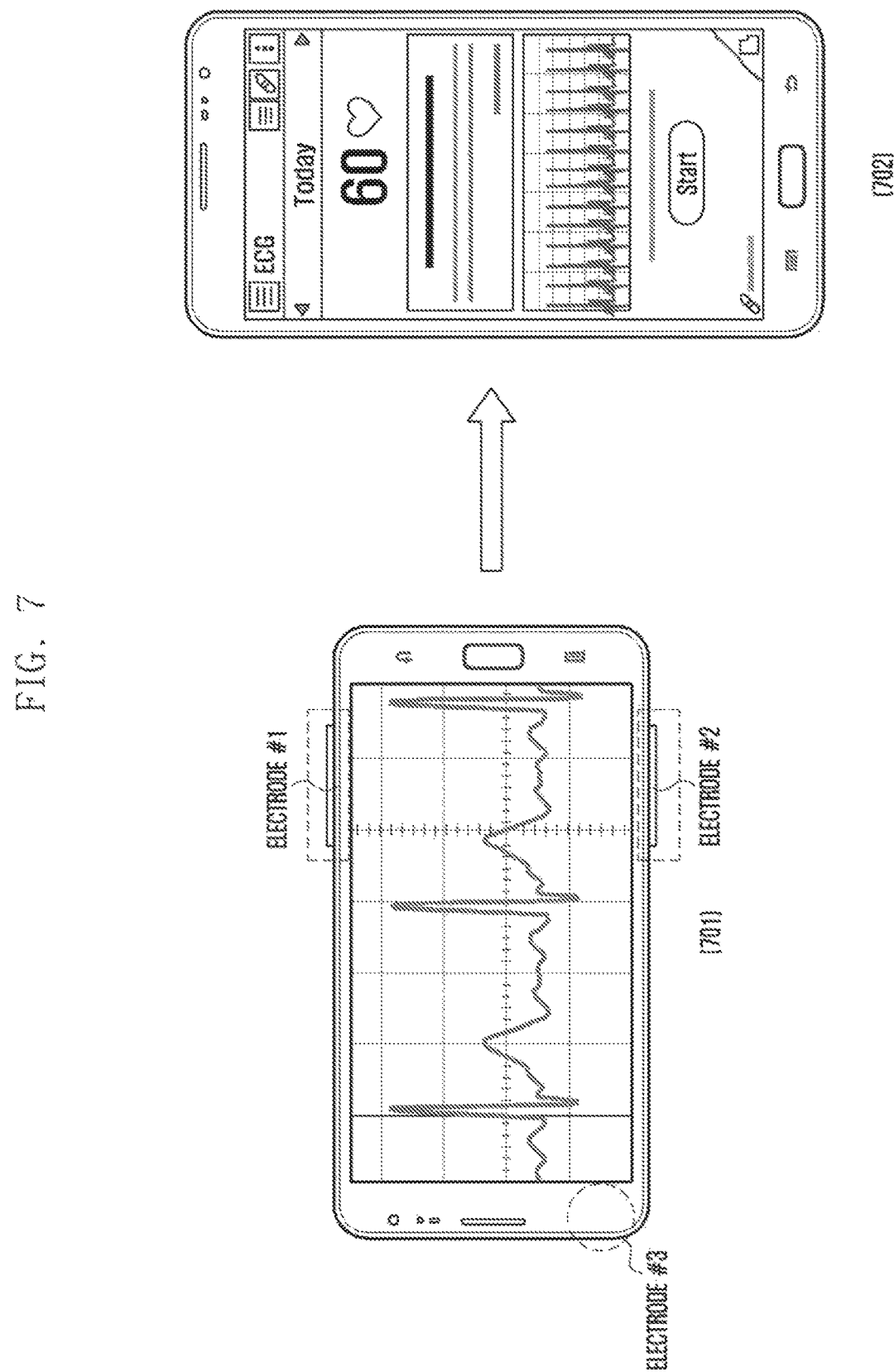
FIG. 7 illustrates an example of function control of a biometric input according to various embodiments.

FIG. 7 illustrates an example of function control of a biometric input according to various embodiments.

Referring to FIG. 7, according to various embodiments, when an application (e.g., a health or medical related application) utilizing ECG-based biometric information in response to a ECG signal-based biometric input is activated, an electronic device can make a control to automatically operate the application utilizing the ECG-based biometric information. For example, as illustrated in reference numeral 701, a user can allow the body thereof to come into contact with all ECG electrodes arranged in the electronic device. The electronic device can determine that an ECG signal is a biometric input having biometric characteristics, automatically activate a health care application for managing and measuring the biometric information in response to the determination as illustrated in reference numeral 702. And the electronic device can control to display the activated health care application to a display unit.

Figure 8:
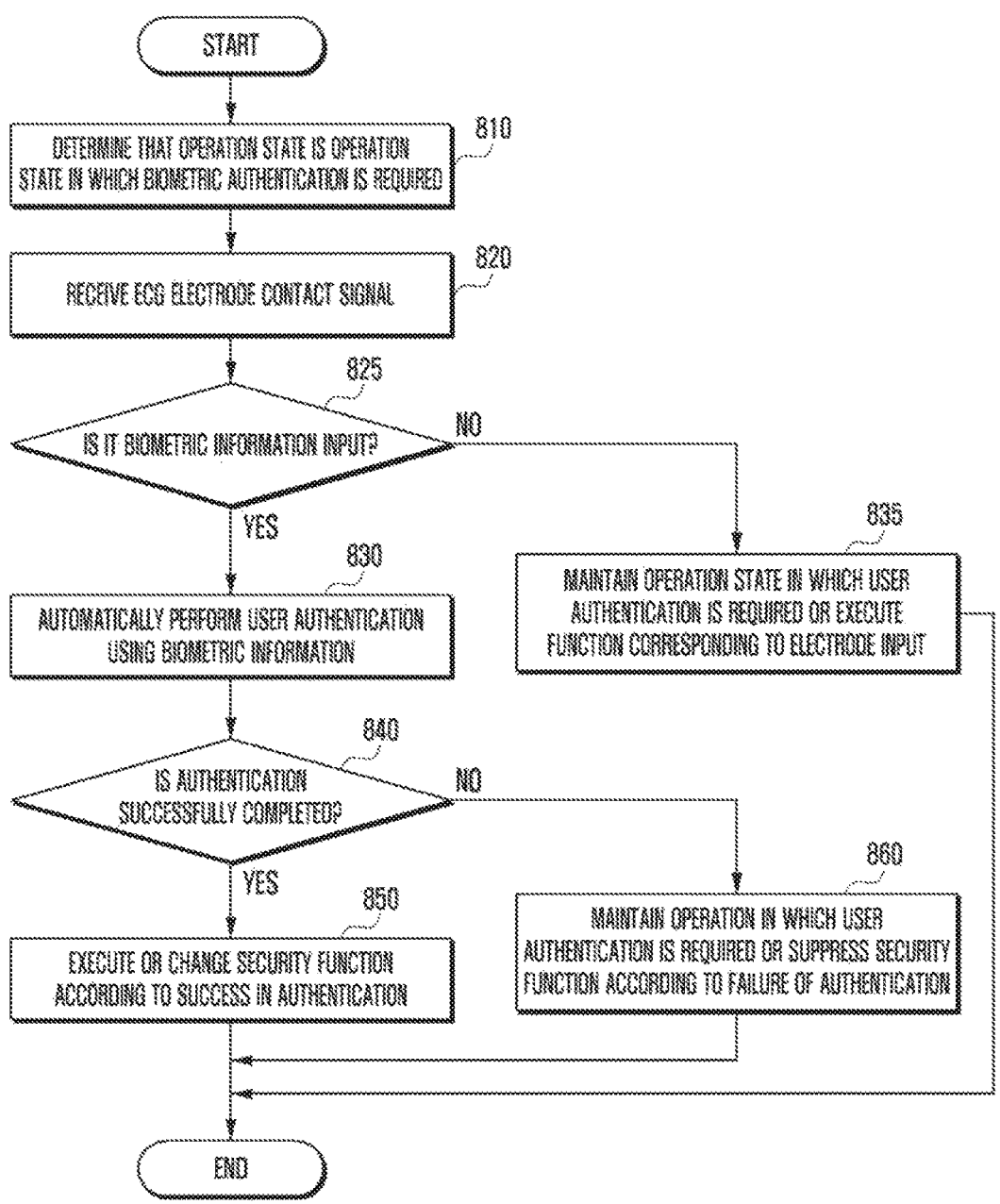
FIG. 8 illustrates a function control method for a biometric input according to various embodiments.

FIG. 8 illustrates a function control method for a biometric input according to various embodiments.

Referring to FIG. 8, according to various embodiments, an electronic device can perform user authentication on the basis of biometric characteristics in response to the ECG signal-based biometric input, and execute a user function or change a right according to a result of the user authentication. Otherwise, the electronic device can restrain a user function or a security function according to failure of the user authentication.

In operation 810, the electronic device determines that an operation state of the electronic device is an operation state requiring user authentication. The operation state requiring the user authentication may be a locking state, a state in which an application requiring user Identification (ID) information is executed, a state in which an application requiring agreement of a user is executed, an electronic payment state, and a state requiring exchange and transmission of privacy information.

The electronic device receives an ECG electrode contact signal according to a body contact through the ECG sensor, in operation 820, and the electronic device determines whether the ECG electrode contact signal is a biometric input which can generate biometric information on the basis of the ECG signal, in operation 825. For example, an ECG pattern, which is biometric information having unique characteristics distinguishable for each user, may be used as information which can identify a user. The electronic device can identify a specific user on the basis of the ECG pattern of the user or feature information (e.g., a waveform, an interest point of the waveform, a heartbeat pattern, and the like) of the ECG signal, so as to provide a user authentication service.

In operation 830, when the ECG signal is a biometric input, the electronic device generates the biometric information in response to the biometric input on the basis of the ECG signal, and performs user authentication on the basis of the generated biometric information. The electronic device can compare the biometric information generated on the basis of the ECG signal with pre-stored biometric information of a user, and determine that the user authentication is successfully completed when the biometric information coincides with the stored biometric information as a result of the comparison.

In operation 850, when the user authentication is successfully completed on the basis of the ECG signal, the electronic device makes a control to execute or change a function of the electronic device according to the success of the user authentication.

In an embodiment, when an ECG signal-based biometric input is detected in a state in which the electronic device is locked, the electronic device performs the user authentication on the basis of the biometric information, and is unlocked when the user authentication is successfully completed. Additionally, when ECG information-based user authentication is successfully completed, the electronic device may automatically operate an application (e.g., a health or medical related application) utilizing the ECG-based biometric information or automatically display a finally-used application on a display unit, according to setting.

In an embodiment, when the electronic device is in an operation state of an application requiring agreement of a user with regard to privacy information, if the ECG information-based user authentication is successfully completed, the electronic device can make a control to perform a user agreement function. For example, the electronic device may be in a state in which an Near Field Communication (NFC) module is functionally connected to a Point of Sales (POS) system of a store for the purpose of product purchase of a user. The electronic device can make a control to perform the user authentication using biometric information when the biometric information is generated through the ECG signal, and permit payment for the product purchase when the user authentication is successfully completed (when the biometric information coincides with pre-stored user biometric information).

In an embodiment, in the electronic device, the user authentication can be required before privacy information is exchanged between different applications or between the electronic device and the server. When the electronic device is in an operation state for asking an agreement for transmitting and exchanging privacy information, the electronic device can make a control to perform the user authentication through the ECG signal, and to transmit and exchange the privacy information when the user authentication is successfully completed.

Meanwhile, in operation 835, when the ECG electrode contact signal is in an electrode input which cannot generate biometric information, the electronic device may maintain a state in which the user authentication is required or may perform a general function corresponding to the electronic input.

In operation 860, when the ECG-based user authentication fails, the electronic device maintains an unlocked state or suppresses a user function or a security function. Otherwise, when the user authentication fails, a control can be made to suppress the electronic device to be used temporarily during a specific period, or suppress a security function in which the user authentication is required and use commonly-used data irrelevant to the user authentication.

Figure 9:
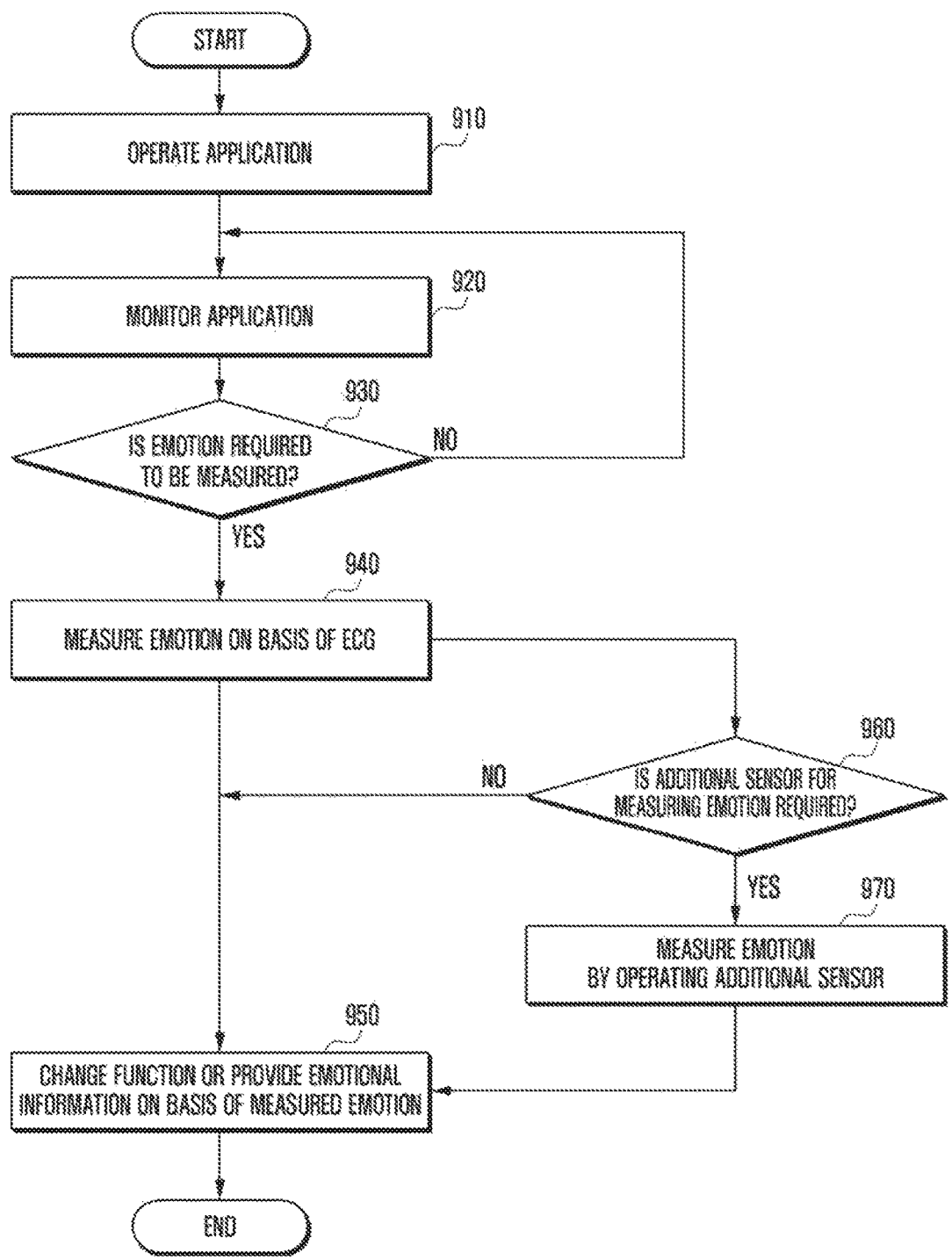
FIG. 9 illustrates a method of controlling a function of a biometric input according to various embodiments.

FIG. 9 illustrates a method of controlling a function of a biometric input according to various embodiments.

Referring to FIG. 9, according to various embodiments, an electronic device can make a control to analyze emotional information of a user using biometric characteristics in response to an ECG signal-based biometric input, and change a function of an application or provide an emotional information function by applying the analyzed emotional information to an application being running.

In operation 910, the processor operates an application and a function utilizing emotional information in response to a user request or a preconfigured electrode input. For example, an application utilizing the emotional information may include a messenger, a video call, an e-mail, a game, and the like, and the present disclosure is not limited thereto.

In operation 920, the processor monitors an application being running. For example, the processor can perform monitoring to analyze the context of a user in a message (or an e-mail) or perform monitoring to analyze a facial expression, a voice, and a voice tone of the user during a video call (or a game).

The processor determines whether emotion is required to be measured at monitoring of the application, in operation 930, and the processor generates emotional information on the basis of an ECG, in operation 940. For example, when it is determined that a text (e.g., joy, fun, pleasant, happy, angry, sad, and the like) indicating emotion of a human among texts which a user inputs in a text input mode is input, a user inputs a text while holding the electronic device using both hands thereof, or the facial expression of the user is changed during a video call, the processor can determine that the emotion is required to be measured.

According to an embodiment, when the emotion is required to be measured, the processor can make a control to activate the biometric sensor, and receive the biometric information from the biometric sensor so as to measure a current emotional state of the user.

In operation 950, the processor changes a function or provides emotional information by reflecting a current emotional state to an application being currently running, on the basis of the measured emotional state of the user.

According to an embodiment, the processor can change an environment (e.g., a background screen, a background music, and the like) of a message application in reflection of the emotional state of the user, or execute a function of recommending an emoticon according to the emotional state.

According to an embodiment, the processor can recommend an emoticon on a screen or change a facial expression of an avatar according to the emotion of the user during the video call.

According to an embodiment, the processor can make a control to change the background color of a screen or recommend a word according to the emotion of the user when the body text of an e-mail is written.

Additionally, in operation 960, the processor determines whether emotional information is required in addition to the measuring of the emotion on the basis of an ECG. When measuring the emotion on the basis of different biometric information is required or it is impossible to measure the emotion on the basis of ECG information, the processor can measure the emotion by operating another biometric sensor in operation 970. For example, the processor can acquire an image of the user through a camera so as to measure emotion of the user on the basis of a facial expression, the shape of the eyes, and the shape of the mouth of the user, or acquire voice of the user through a microphone so as to measure the emotion of the user on the basis of voice, an accent, a tone, and used words. Further, the processor can additionally measure the emotion of the user through a heart rate while activating an HR sensor. In this case, the electronic device can measure the emotion through another biometric sensor in addition to the measuring of the emotion on the basis of an ECG, thereby enhancing the accuracy of emotional information of the user.

FIGS. 10A to 10D illustrate examples of function control of a biometric input according to an embodiment.

Figure 10A:
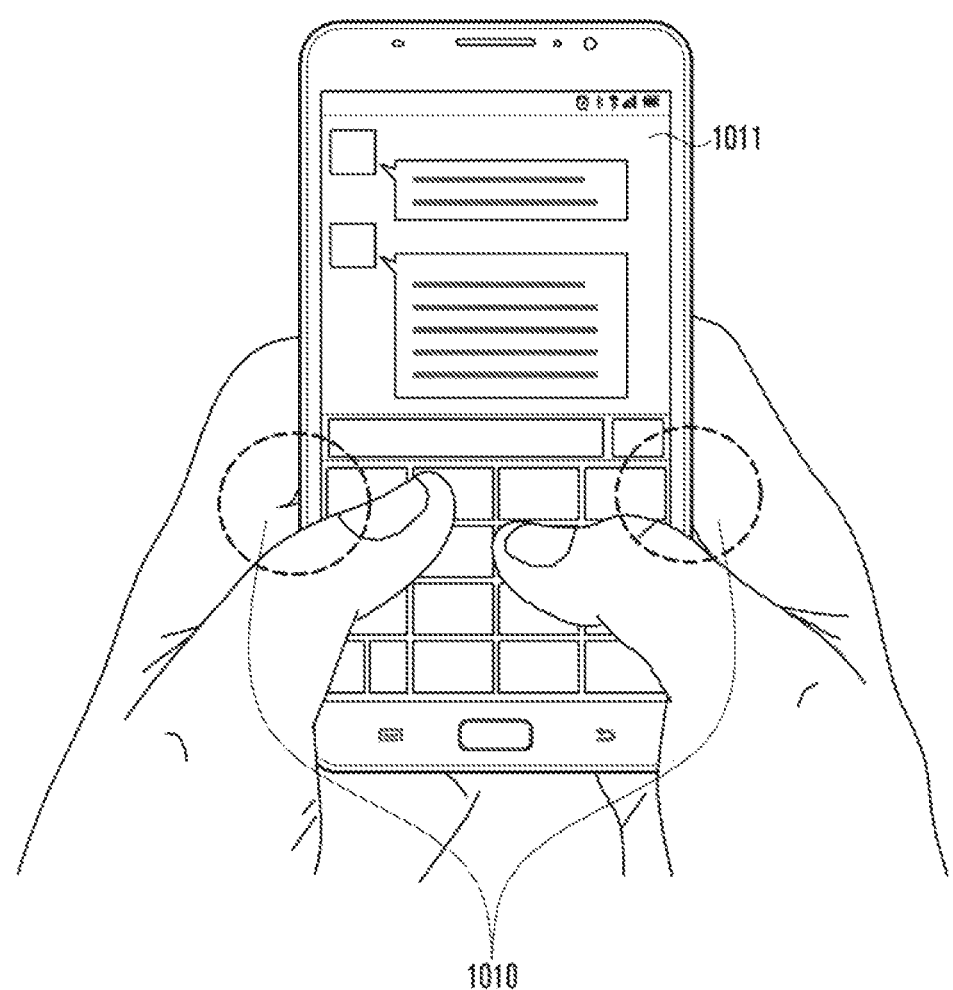
Figure 10C:
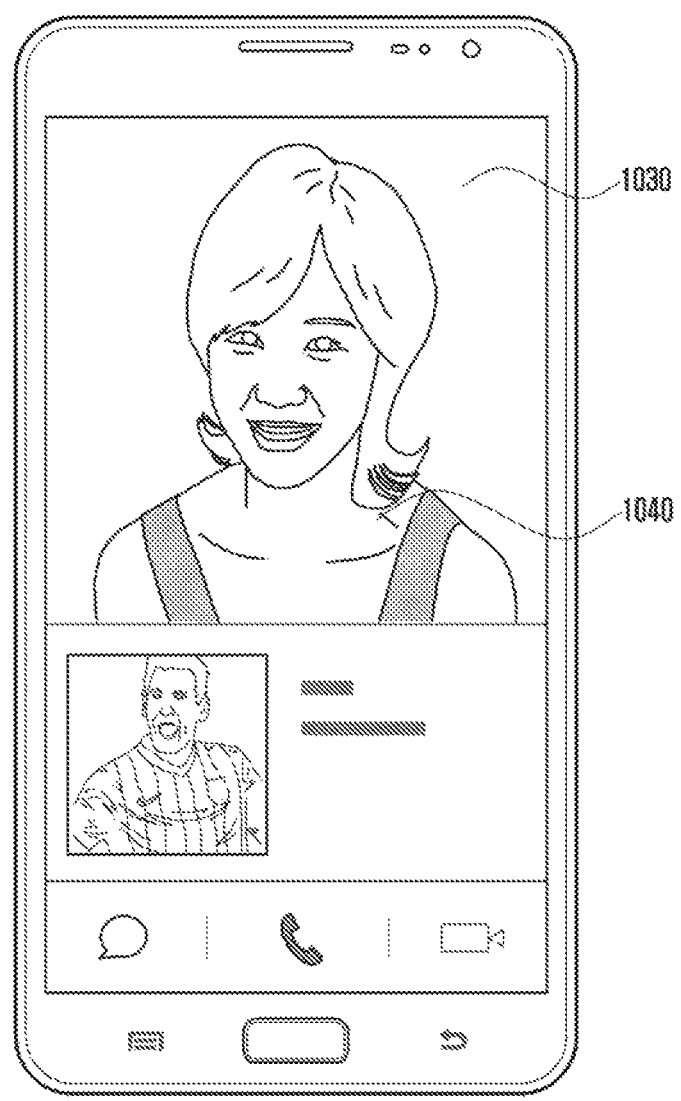

Referring to FIG. 10A, according to various embodiments, the electronic device can make a control to determine emotional information of a user in response to an ECG-based biometric input, and automatically change the color of a background screen according to the emotional information of the user. The user can input a text character through a messenger application. At this time, the user may input a text character while holding the electronic device with both hands thereof. In this case, the electronic device can operate an ECG sensor according to the holding of the electronic device with both hands, receive an ECG signal from ECG electrodes 1010 arranged on both sides of the electronic device, and generate a meaningful ECG value from the ECG signal.

The electronic device can determine the emotion of the user on the basis of biometric information generated from the ECG electrodes 1010 arranged on the both sides of the electronic device. For example, the electronic device can classify the ECG value into various levels according to a predetermined criterion, and the color of an image can be set according to the levels.

The electronic device can make a control to determine the level according to a change in the ECG value of the user while inputting a text, and automatically change the color of the background screen 1011 of a messenger application according to emotion corresponding to the level. For example, when the heartbeat of the user increases while a text is input, the electronic device can make a control to determine that the emotion of the user is in an excited state by analyzing the heart beats, and automatically change the background screen from the blue color to the red color in order to reflect the emotional state of the user.

Referring to FIG. 10B, the electronic device according to various embodiments can determine emotional information of a user in response to an ECG-based biometric input and execute an emoticon recommendation function corresponding to the emotion of the user according to the emotional information of the user. The user can input a text in a state in which both hands thereof are in contact with ECG electrodes 1020 arranged in the electronic device.

When a meaningful ECG value is generated on the basis of the ECG signal while the user inputs the text, or when it is identified through analyzing the text of the user that a word indicating emotion of the user is input, the electronic device can analyze an emotional state of a user on the basis of a body contact signal of the ECG electrodes 1020 arranged in the electronic device. The electronic device can provide a recommendation emoticon 1021 corresponding to current emotion of the user in reflection of the analyzed emotional state of the user. For example, the electronic device can make a control to recommend an emoticon of an angry face on the messenger application when emotional information of the user is an angry state, recommend an emoticon of a sad face on the messenger application when the emotional information of the user is a sad state, and recommend an emoticon of a surprised face on the messenger application when the emotional information of the user is a surprised state, on the basis of the ECG value.

Referring to FIG. 10, the electronic device according to various embodiments can determine the emotional information of the user in response to an ECG-based biometric input at a video call, and provide an avatar in reflection of the emotional information of the user or provide the emotional information of the user on a video call screen. For example, the electronic device can support a function of providing another replacement image 1040 (e.g., a virtual graphic content, i.e., an avatar, used as an alter ego of the user on a cyber space) in addition to a photographing image of the user for the purpose of personal privacy during the video call. Here, the avatar can be provided in substitution of an image of the user during the video call. The electronic device may provide the image of the user during the video call or provide both the image of the user and the avatar according to the request or the setting of the user. The electronic device can make a control to determine emotional information of the user during the video call and change a facial expression of the avatar on the basis of the emotional information of the user.

In an embodiment, the electronic device can analyze a facial expression of the user from an image photographed during the video call, and voice, accent, tone, and the like of the user from recorded voice, so as to additionally measure emotion of the user, and improve the reliability when the current emotion of the user is analyzed.

In another embodiment, the electronic device can make a control to change the background color of a video call screen 1030 according to a current emotional state of the user on the basis of the emotional information of the user during a video call.

Figure 10D:
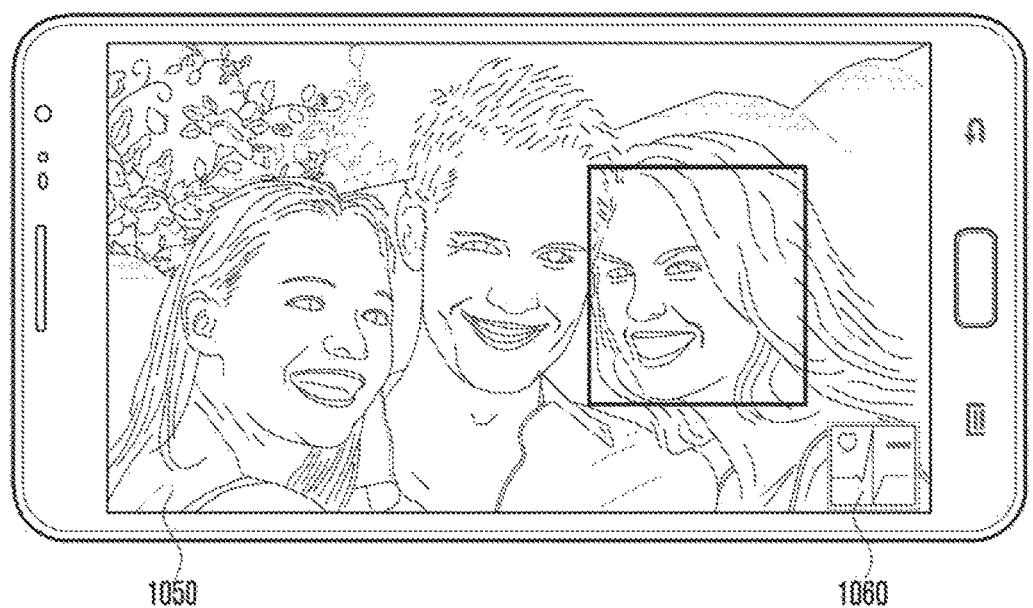

Referring to FIG. 10D, when ECG-based biometric information is generated, the electronic device according to various embodiments can make a control to grant information (e.g., the number of heart beats, an ECG waveform, and HRV-based emotional information) related the biometric information as an image, or grant the emotional information as tag information of the image.

The electronic device can generate the biometric information by analyzing an ECG signal received from ECG electrodes in a camera application operated state, and when an image is shot, display the generated biometric information 1060 on the shot image 1050. Otherwise, the electronic device can make a control to store the generated biometric information in a metadata region (e.g., exif of JPEG) of the shot image.

According to an embodiment, the electronic device can perform user authentication by performing a face recognition function on an image shot through a camera, and store biometric information generated in association with a face recognized image. For example, the electronic device can recognize a user thereof by performing face authentication on the basis of an image acquired from a self-camera (e.g., the front camera) (e.g., comparing the similarity with information related to a face image of a user pre-stored in a face recognition module through the electronic device or an external device functionally connected thereto). The electronic device can display the recognized face of a user and the generated biometric information to be associated with each other, or store the recognized face of a user and the generated biometric information in a metadata region to be associated with user identification information.

According to another embodiment, when user information obtained through face recognition corresponds to a user recognized through biometric information recognition, the electronic device can store the biometric information and a minimum part (e.g., region identification information of the corresponding user) of a shot image to be associated with each other.

According to another embodiment, the electronic device can recognize an emotional state of the corresponding user through the biometric information, and change a facial expression of the user within the shot image or change an attribute (e.g., the brightness, the tone, and the resolution) of the shot image. For example, the electronic device can change an expressionless face of the user in the shot image to a smiling expression on the basis of the biometric information. As another example, when it is determined on the basis of the biometric information that the emotion of the user is in a happy state, the electronic device can make a control to change the shot dark image to a bright image. Further, when it is determined on the basis of the biometric information that the emotion of the user is in a sad state, the electronic device can make a control to assign a rainy effect or a water forming effect to a landscape picture shot during the daytime of a sunny day.

Electrode Input Embodiment

FIG. 11 illustrates an example of function control of an electrode input according to various embodiments.

Referring to FIG. 11, an electronic device according to various embodiments can activate a preconfigured application in response to a body contact with one or more electrodes of the ECG sensor. In this case, in the electronic device, application triggering preconfigured for each electrode contact condition and each operation state of the electronic device may be different.

For example, when a meaningful ECG value cannot be acquired by signals of the ECG electrode generated by a body contact, the electronic device can determine the signals as an electrode input, and identify a detection condition of a body contact signal. For example, three ECG electrodes are arranged in the electronic device. The electrode #1 1110 may be arranged on the rear surface of the electronic device, and electrodes #2 and #3 1120 and 1130 may be arranged on the lower side surface of the electronic device.

As illustrated in a of FIG. 11, a user can be in contact with the electrode #1 1110 arranged on the rear surface of the electrode. The electronic device can make a control to execute a first application (e.g., a messenger application) mapped to the electrode #1 1110 in response to an electrode input based on a contact with the electrode #1 1110. When the body of the user is in contact with the electrode #2 1120 and the electrode #3 1130, the electronic device can make a control to execute a second application (e.g., the camera application) mapped to correspond to the contacts with the electrode #2 1120 and the electrode #3 1130. When one hand of the user comes in contact with the electrode #2 1120 and the electrode #3 1130, the electronic device cannot generate the biometric information so as to determine that a contact signal is an electrode input. When the body of the user is in contact with the electrode #3 1130, the electronic device can make a control to execute a third application (e.g., a schedule application) mapped to correspond to the body contact with the electrode #3 1130.

Figure 12:
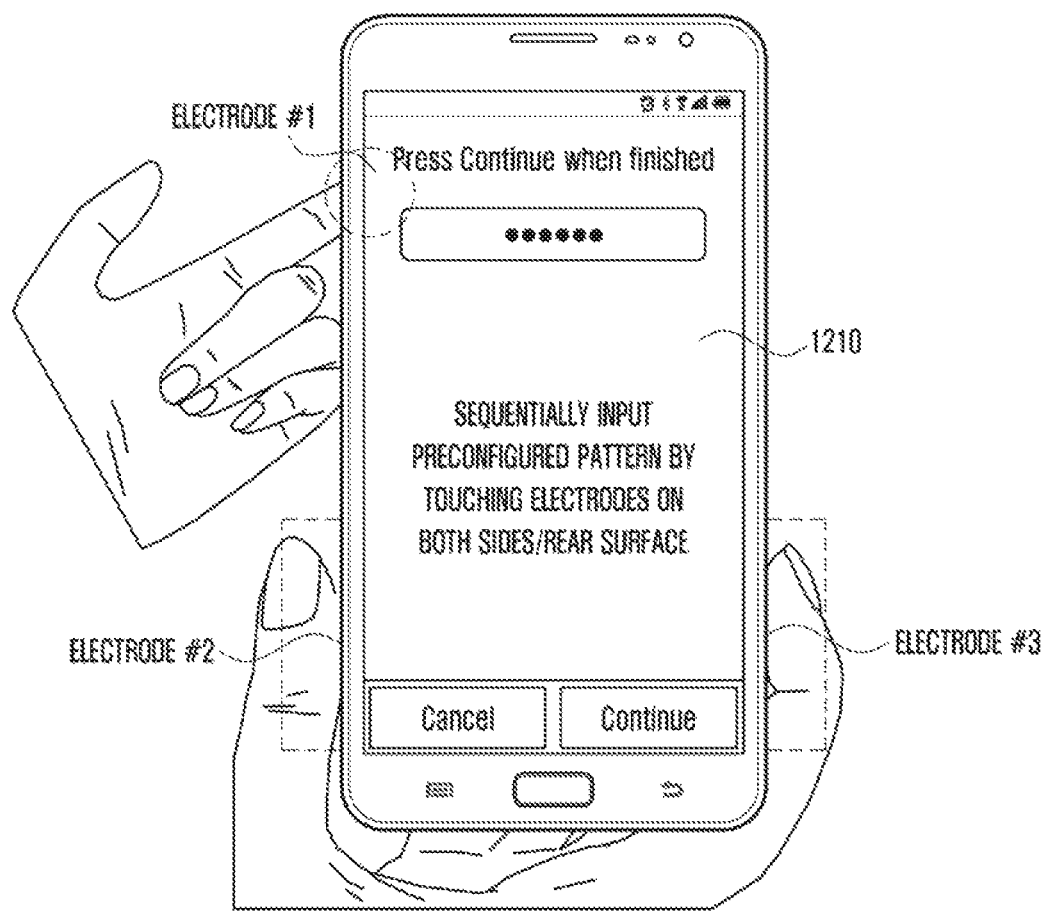
FIG. 12 illustrates an example of a function control of an electrode input according to various embodiments.

FIG. 12 illustrates an example of a function control of an electrode input according to various embodiments.

Referring to FIG. 12, according to various embodiments, an electronic device can support a password input function for a security function by mixing body contact positions and a contact sequence of electrodes using a plurality of ECG electrodes. The electronic device can operate in a state in which an application requiring user authentication is executed. For example, the electronic device can display a password input screen 1210 on a display unit. A user can make the body be in contact with the ECG electrode so as to input a password. First, the user can make the body thereof be in contact with the electrode using a finger in a sequence of attachment/detachment to/from the electrode #2, attachment/detachment to/from the electrode #2, attachment/detachment to/from the electrode #1, attachment/detachment to/from the electrode #3, attachment/detachment to/from the electrode #2, and attachment/detachment to/from the electrode #1. Then, the electronic device can determine that the password is input, on the basis of the sequence of #2, #2, #1, #3, #2, and #1 according to the body contact positions and the contact sequence. When the password obtained by the ECG electrode coincides with a preconfigured electrode sequence of a password, the electronic device is unlocked or a function of the electronic device is unlocked.

Figure 13:
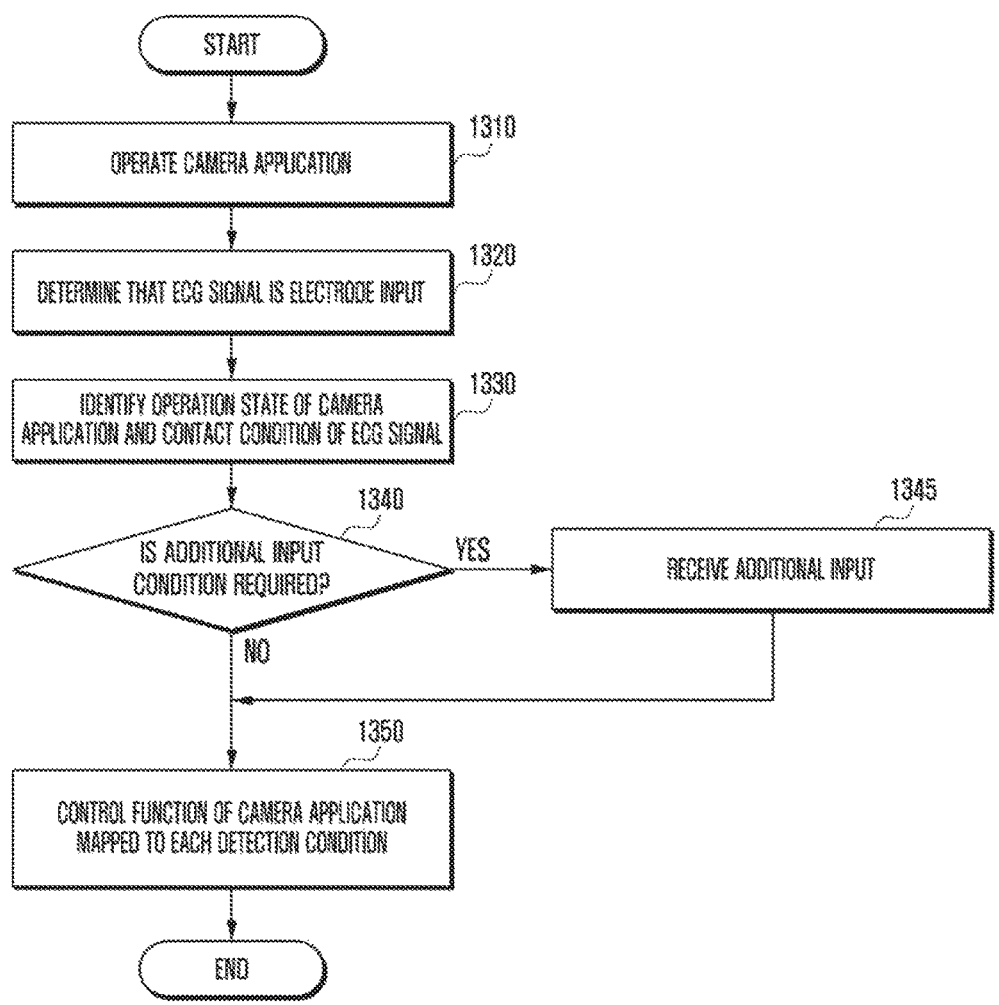
FIG. 13 illustrates a method of controlling a function of an electrode input according to various embodiments.

FIG. 13 illustrates a method of controlling a function of an electrode input according to various embodiments.

Referring to FIG. 13, according to various embodiments, an electronic device can shoot an image or a video in response to the electrode input on the basis of at least one ECG signal, and control a camera application related thereto.

In operation 1310, a processor of the electronic device operates the camera application. In operation 1320, the processor receives an ECG signal, and determines that the ECG signal is an electrode input which cannot generate biometric information. In operation 1330, the electronic device identifies an operation state of the camera application and a body contact condition of the ECG signal. For example, the electronic device can identify which ECG electrode an ECG signal is received from, the number of ECG electrodes from which the ECG signals are received, a body contact time, a detailed function running on the camera application, a setting state of an additional input for executing a function, and the like.

According to an embodiment, when an object contact is detected through the ECG electrode, the electronic device can additionally perform an operation of determining whether an additional condition for performing a shooting operation is input, but the following operations 1340 and 1345 may be omitted.

In operation 1340, the processor determines whether an additional input condition is required for executing a function, and in operation 1350, when the additional input condition is not required, the processor identifies a function of the camera application mapped to a contact detection condition in response to an electrode input based on an ECG signal, and controls the identified function of the camera application.

According to an embodiment, when an ECG signal, which cannot generate the biometric information, corresponds to an attachment operation or a detachment operation, the electronic device can perform a shooting function mapped to the attachment operation or the detachment operation.

According to an embodiment, the electronic device may perform a shooting operation when detecting, through the ECG signal, a state change from a non-contact state to a contact state or a state change from a contact state to a non-contact state. For example, when at least one of the ECG electrodes is changed from a non-contact state to a contact state in a state in which the camera application is operated, the electronic device may perform a shooting command on the basis of a change of the received ECG signal. As another example, the electronic device may perform a shooting command when change to the non-contact state is detected in a state in which the camera application is operated and a contact is maintained through the ECG electrode. Here, the ECG signal may be a predetermined signal range value according to a body contact of a person.

When an additional input condition for executing a camera function is required in operation 1340, the processor receives an additional input, in operation 1345. Next, the processor proceeds to operation 1350 in response to the reception of the additional input. Here, operation 1340 may be omitted.

Hereinafter, examples of electrode inputs based on various ECG signals will be described in order to perform a shooting command of the camera application, and a contact detection condition for performing the shooting command may be configured variously, e.g., configured by a user or configured during a manufacturing process.

According to an embodiment, when an ECG electrode is arranged or embedded in a hardware button or a key, if a body contact is maintained at the ECG electrode and an additional input condition, e.g., an input (the key "down" or the key "up") related to the hardware button is detected, the electronic device can perform the shooting command.

According to another embodiment, when an attachment operation is performed on any one ECG electrode, and an additional input condition, e.g., a condition in which a contact state is maintained for a predetermined time (e.g., 1 second) or longer, the electronic device can perform the shooting command.

According to another embodiment, when it is detected that an ECG electrode is switched from a non-contact state to a contact state, the electronic device may perform the shooting operation. In this case, when the non-contact state is not maintained for a predetermined time or longer, the electrode device can make a control to not generate the shooting operation even when a contact with a specific ECG electrode is detected.

According to another embodiment, after white-balancing or auto-focusing is completed in the non-contact state, when a condition is satisfied in which a contact with the ECG electrode is detected, the electronic device can perform the shooting operation.

According to various embodiments, when it is configured to perform the shooting command through a plurality of means (e.g., a biometric sensor and a gesture (or pose) sensor), if an electrode input of the biometric sensor is detected according to the priority of the biometric sensor, the electronic device can perform the shooting operation. For example, the electronic device can make a control to ignore the shooting command generated by a gesture or a pose from a time point when an object comes into contact with one or more of the ECG electrodes to a time point when the object is detached from the one or more of the ECG electrodes.

Figure 14:
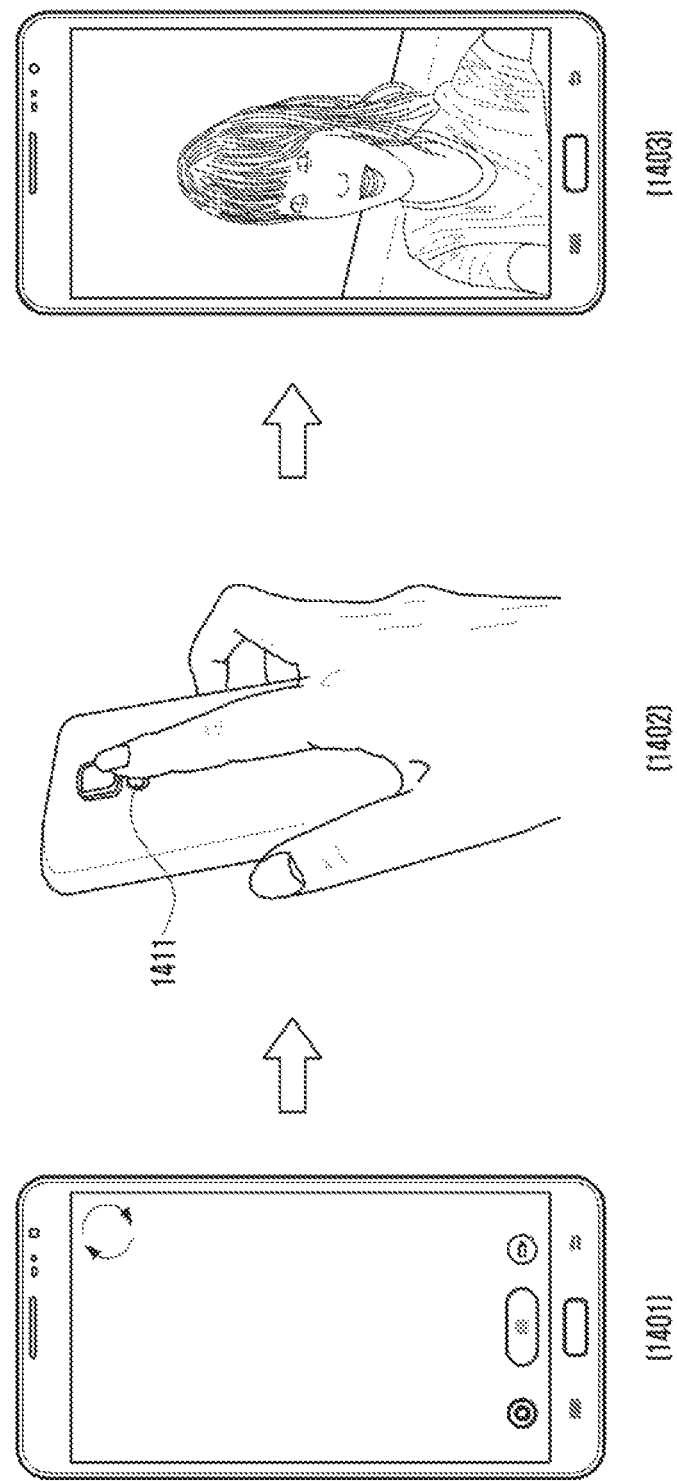
FIG. 14 illustrates an example of function control of an electrode input according to various embodiments.

FIG. 14 illustrates an example of function control of an electrode input according to various embodiments.

Referring to FIG. 14, a user of an electronic device can shoot (e.g., self-shoot) an image thereof using the front camera of the electronic device. The user can shoot an image or a video using the ECG sensor when attempting to shoot an image of the user using the front camera.

The electronic device can operate a camera application in a state in which the ECG sensor is operated, as illustrated in reference numeral 1401. In this case, the user can make a control to activate the front camera of the electronic device. Next, as illustrated in reference numeral 1402, the user can make a finger thereof come into contact with (or be detached from) an ECG electrode 1411 arranged on the rear surface among the ECG electrodes arranged in the electronic device, in order to shoot an image of the user.

The electronic device can detect a body contact signal from the ECG electrode 1411 and determine that the body contact signal is an electrode input, so as to perform the shooting operation (e.g., image shooting or video shooting) in response to the electrode input, as indicated by reference numeral 1403. Accordingly, the user can easily control shooting by one hand using the ECG electrode arranged in the electronic device, without an input for a separate shooting button for camera shooting.

According to an embodiment, the electronic device may make a configuration to perform a start shooting operation using electrodes of the biometric sensor arranged in a direction different from an arrangement direction of operated (activated) cameras, but may shoot an image using electrodes of the biometric sensor arranged in a direction identical to the arrangement direction of the cameras.

Figure 15:
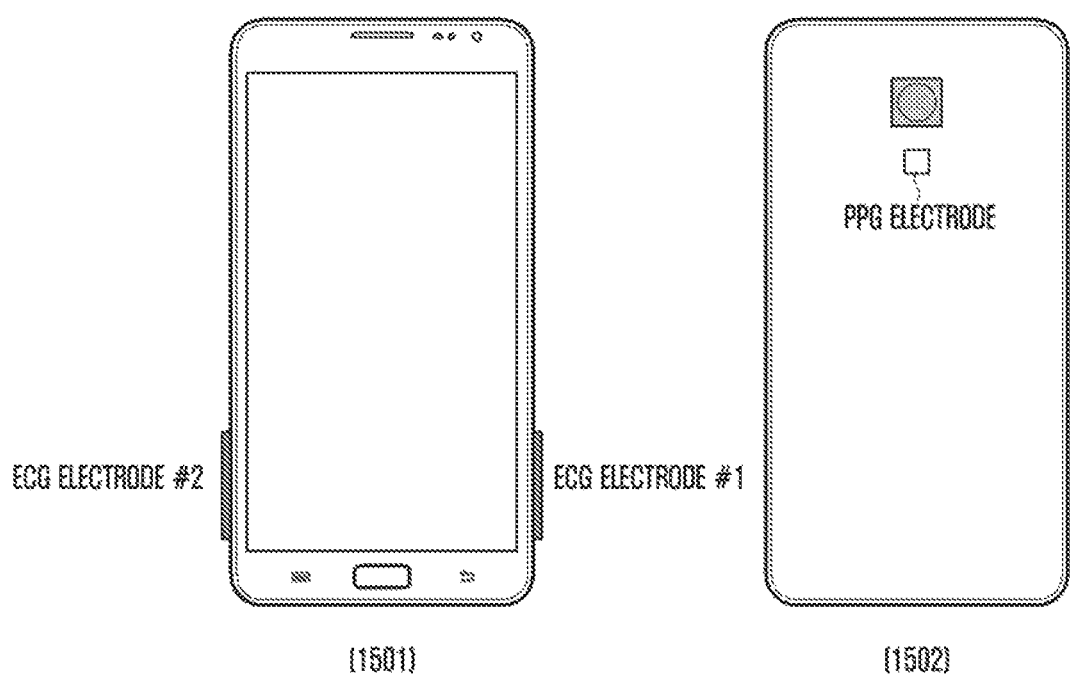
FIG. 15 illustrates an example of a function control of an electrode input according to various embodiments.

FIG. 15 illustrates an example of a function control of an electrode input according to various embodiments.

Referring to FIG. 15, according to various embodiments, when there are at least two biometric sensors or electrodes, an electronic device can variously control a function of a camera application according to positions of the electrodes of the biometric sensor, in which a signal is detected.

According to an embodiment, the electronic device can make a control to operate different cameras according to the positions of electrodes in which contacts are detected, among the ECG electrodes. For example, operated cameras may be changed according to a body contact electrode in the electronic device in which an ECG sensor and a PPG sensor are installed. For example, electrodes of the ECG sensor may be arranged on both sides of the electronic device, as illustrated in reference numeral 1501, and electrodes of the PPG sensor may be arranged on the rear surface of the electronic device, as illustrated in reference numeral 1502.

The electronic device can make a control to operate a front camera when a body contact or detachment operation based on the electrodes of the PPG sensor is detected while a camera application is operated. The electronic device can make a control to operate a rear camera (e.g., display a preview or perform a shooting operation) when a body contact or detachment operation based on the electrodes of the ECG sensor is detected.

Figure 16:
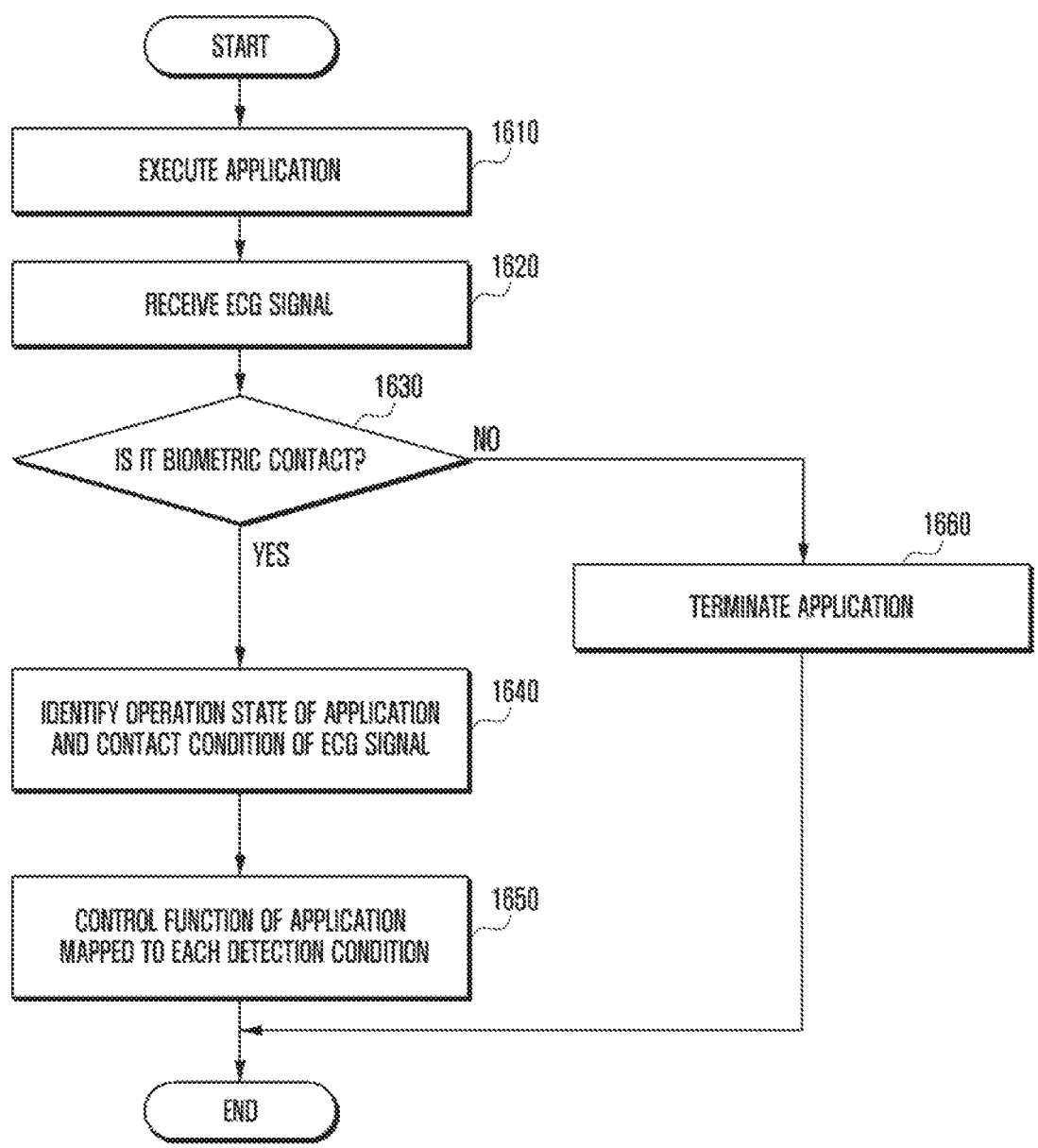
FIG. 16 illustrates a method of controlling a function of an electrode input according to various embodiments.

FIG. 16 illustrates a method of controlling a function of an electrode input according to various embodiments.

Referring to FIG. 16, a processor of an electronic device determines that an operation state of the electronic device is an application executing state, in operation 1610. In operation 1620, the processor receives, from an ECG electrode, an ECG signal (e.g., a body contact signal) not including biometric characteristics. In operation 1630, the processor determines, through the ECG signal, that an object contacting the ECG electrode is a body (e.g., a finger). For example, the processor can determine whether the contacting object is a body, according to whether a waveform of the ECG signal has characteristics of an ECG waveform of a human.

In operation 1640, when the ECG signal corresponds to a body contact, the processor identifies an operation state of an application and a body contact condition. In operation 1650, the processor can control a function of the application mapped to each body contact condition. For example, when an ECG signal received from a specific ECG electrode corresponds to a body contact, the processor can execute a shooting command (operation).

In operation 1660, when the ECG signal does not correspond to the body contact, the processor executes an application terminating function. For example, when an object such as a table or a wall rather than the body is in contact with the ECG electrode, the processor may not execute the shooting operation or terminate (or pause) the camera application.

Figure 17:
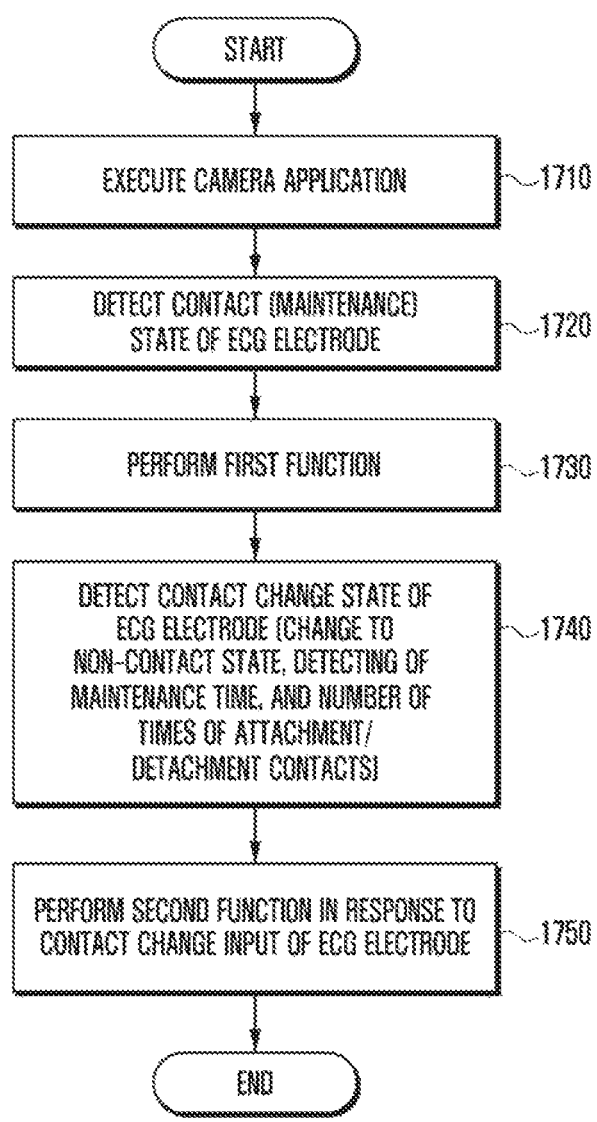
FIG. 17 illustrates a method of controlling a function of an electrode input according to various embodiments.

FIG. 17 illustrates a method of controlling a function of an electrode input according to various embodiments.

Referring to FIG. 17, a processor of an electronic device determines that an operation state of the electronic device is an application executing state, in operation 1710. The processor determines an electrode-specific contact state through an ECG sensor. In operation 1720, the processor detects a body contact state on the basis of an ECG signal (e.g., a body contact signal) received from an ECG electrode. In operation 1730, the processor makes a control to perform a first function of an application being running, in response to the body contact state.

In operation 1740, the processor detects a body contact change state on the basis of the ECG signal, and in operation 1740, the processor makes a control to perform a second function of the application being running, in response to the body contact change state. For examples, The body contact change state may include a change from a contact state to a non-contact state (e.g., detachment), a state in which the body contact state is maintained for a predetermined time (e.g., the body contact is maintained for 1 second or longer), and a state in which a position of the body contact or a non-contact electrode is changed.

According to an embodiment, the electronic device can perform an auto-focusing function or a half-shutter function when a camera application is being operated and a body comes into contact with an ECG electrode in a state in which a preview screen is displayed, and can perform a shooting command when a state of the ECG electrode is changed from the body contact state to the non-contact state.

According to an embodiment, in the electronic device, electrodes of an ECG sensor are arranged on some of the front surface, the bezel, the rear surface, and the side surface of the electronic device, or an ECG electrode may be configured to include an internal hardware key or a button. The electronic device can perform a first function when a body contact is detected in the ECG electrode installed in the corresponding key or the button, perform a second function when an input operation (down or up) of the key or the button is detected, and perform a third function when a change of a state of the key or the button to a body non-contact state is detected. Here, the first function may be a half-shutter function of a camera, the second function may be a shooting function, and the third function may be a function of activating a menu selection of an camera application. Otherwise, the first function may be an ECG measuring function of the ECG sensor, the second function may be the shooting function, and the third function may be a function of editing (e.g., synthesizing and image-deforming) a shot image on the basis of ECG information. Otherwise, the first function may provide one or more of function selection using GUI of the camera and a focus position moving function, the second function may be the half-shutter function (one or more of a focus fixing function, an auto-focusing function, and an exposure control function), and the third function may be the shooting function.

According to an embodiment, the electronic device can perform different functions according to a contact maintenance time after the contact is detected in the ECG electrode. For example, the electronic device can perform the first function when the contact maintenance time measured from a contact of the ECG electrode to detachment thereof is equal to or lower than a first maintenance time (e.g., 0.1 second), and can perform the second function when the contact maintenance time is higher than the first maintenance time. In this case, the first function according to the contact maintenance time may be a snap picture shooting function, and the second function may be a beauty shop shooting function. Further, when the contact maintenance time increases higher than the first maintenance time, the electronic device may be performed the third function in accordance with (e.g., in proportion to, in inverse proportion to, in time to, and the like) the increased maintenance time. For example, the electronic device can, when the contact maintenance time exceeds the first maintenance time, perform a function of selecting a beauty shop function, adjust the number of times, the range, the intensity, and the like of the third function (e.g., blemish removal, a blurring effect, an out-of-focus, and the like) in proportion to the maintenance time after the exceedance, and display a preview, and when detachment is performed, store the corresponding image in a memory.

According to another embodiment, the electronic device can differently apply a shooting mode by measuring the number of times by which a detachment operation is repeatedly performed within a predetermined time after an object comes into contact with the ECG electrode. For example, the electronic device can make a control to perform shooting in an HDR mode when a body contact state and a detachment state are repeatedly performed in the ECG electrode twice within 3 seconds, and to perform shooting by switching to a night shooting mode when the body contact state and the detachment state are repeatedly performed in the ECG electrode three times.

Figure 18:
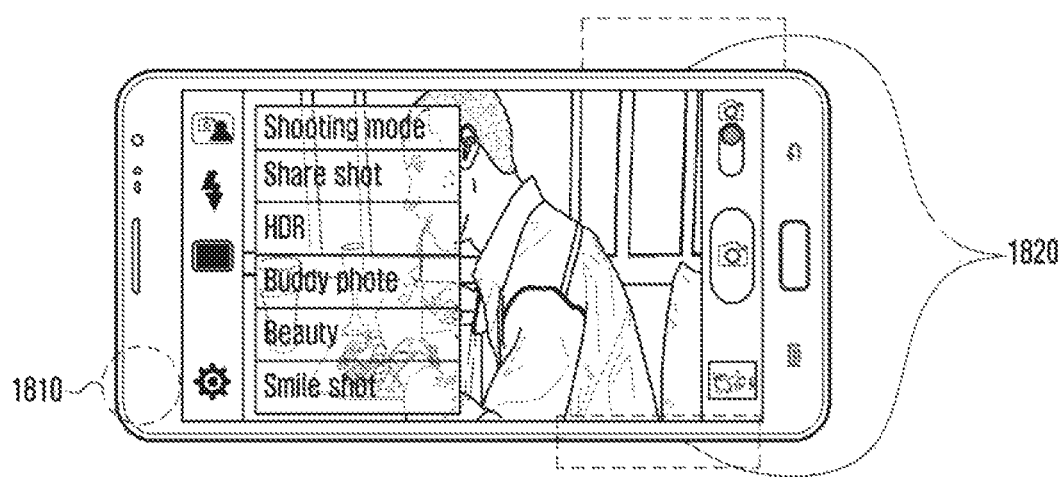
FIG. 18 illustrates an example of function control of an electrode input according to various embodiments.

FIG. 18 illustrates an example of function control of an electrode input according to various embodiments.

Referring to FIG. 18, the electronic device can execute a camera mode changing function in response to an electrode command based on a part of ECG electrodes, and execute a camera shooting operation in response to an electrode command based on the other parts of the ECG electrodes.

The electronic device can execute a function of performing a shooting function when the camera application is operated in a shooting mode and a body comes into contact with an ECG electrode 1810, and selecting a camera mode using ECG electrodes 1820 arranged on both sides when the camera application is operated in a camera mode selecting operation state and the body comes into contact with the ECG electrodes arranged on both side ends of the electronic device.

In this case, the ECG electrodes 1820 arranged on both side ends may be an input corresponding to an operating input in the upward direction or the downward direction according to a body contact. The electronic device can perform a shooting function on the basis of a selected camera mode when the body comes into contact with or is detached from the ECG electrode 1810 after the user selects a camera mode through the ECG electrodes 1820.

According to another embodiment, the electronic device may perform a shooting function when the body comes into contact with the ECG electrode 1810, and perform a shooting function using a self-camera when the body comes into contact with and is then detached from the ECG electrodes 1820 arranged on both side ends.

Figure 19:
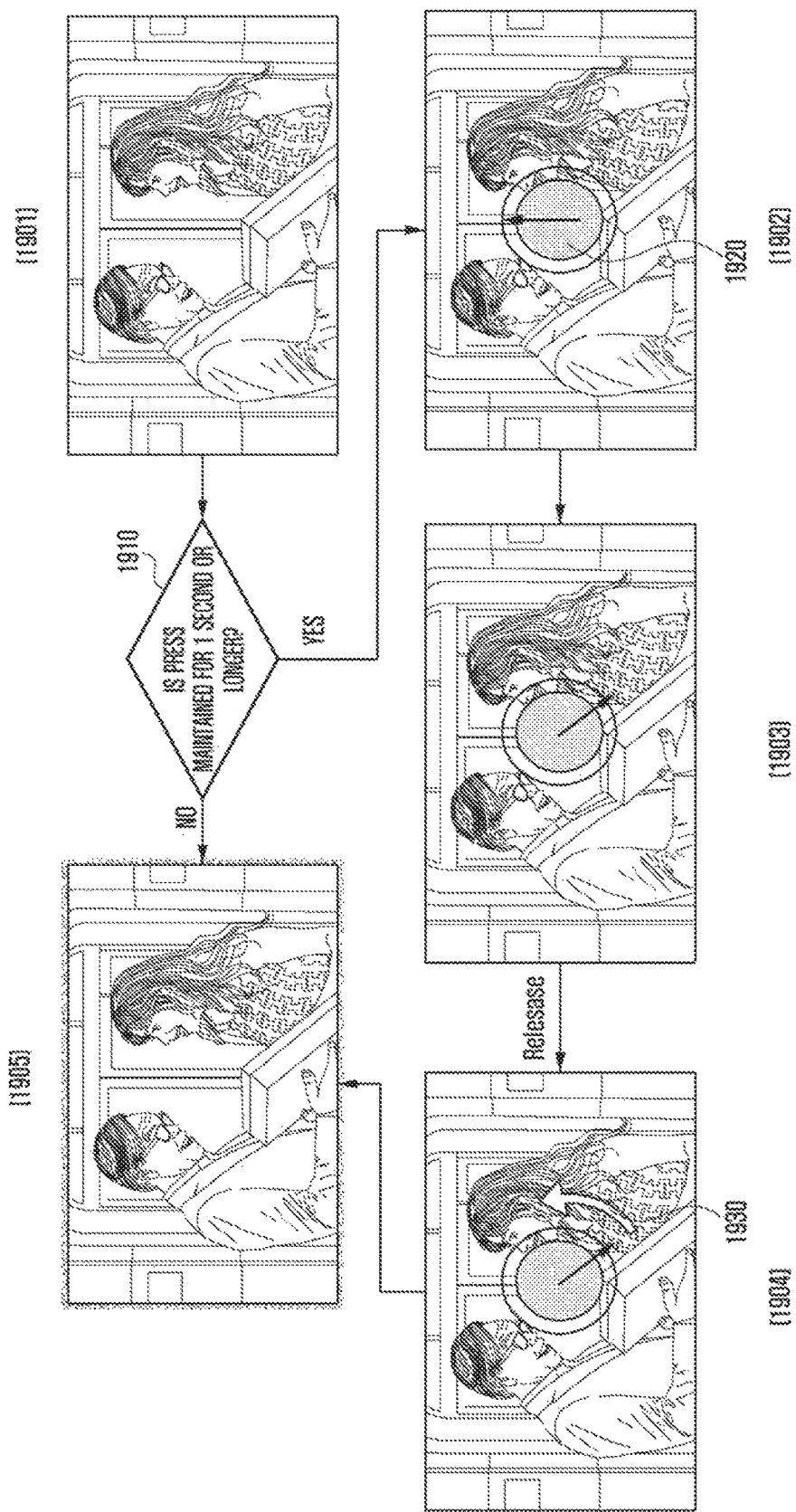
FIG. 19 illustrates an example of function control of an electrode input according to various embodiments.

FIG. 19 illustrates an example of function control of an electrode input according to various embodiments.

Referring to FIG. 19, an electronic device according to various embodiments can control a time setting for shooting a timer according to a body contact maintenance time in response to an electrode command based on an ECG electrode.

For example, the electronic device can operate a camera application so as to provide a preview image to a display unit, as indicated by reference numeral 1901. A user can maintain a body contact with the ECG electrode in a state in which the preview image is displayed. In reference numeral 1910, the electronic device can make a configuration to determine whether an ECG signal is an electrode input and the body contact is maintained for 1 second or longer, perform a picture shooting operation when a detachment state is detected within a contact maintenance time of 1 second, and increase a timer count (time) by 1 per second from a contact occurrence time point up to n seconds when the contact maintenance state is maintained for 1 second or longer. In this state, when the ECG electrode is changed from a body contact state to a non-contact state, the electronic device triggers a shooting function by a configured timer and shoots an image when the configured timer is expired. As illustrated in reference numerals 1902 and 1903, when the body contact with the ECG electrode is maintained for 1 second or longer, the electronic device can provide an indicator 1920 indicating, on the display unit, that the timer is being configured. As illustrated in reference numeral 1904, when the ECG electrode is changed (released) from the body contact state to the non-contact state, the electronic device can provide an indicator 1930 indicating expiration of the configured timer by the body contact. As illustrated in reference numeral 1905, when the configured timer expires due to the body contact, the electronic device can execute a shooting operation in response thereto, and store the same.

According to another embodiment, the electronic device can adjust a video recording time or a temporal length of a voice-recorded content in proportion to a body contact maintenance time.

Figure 20:
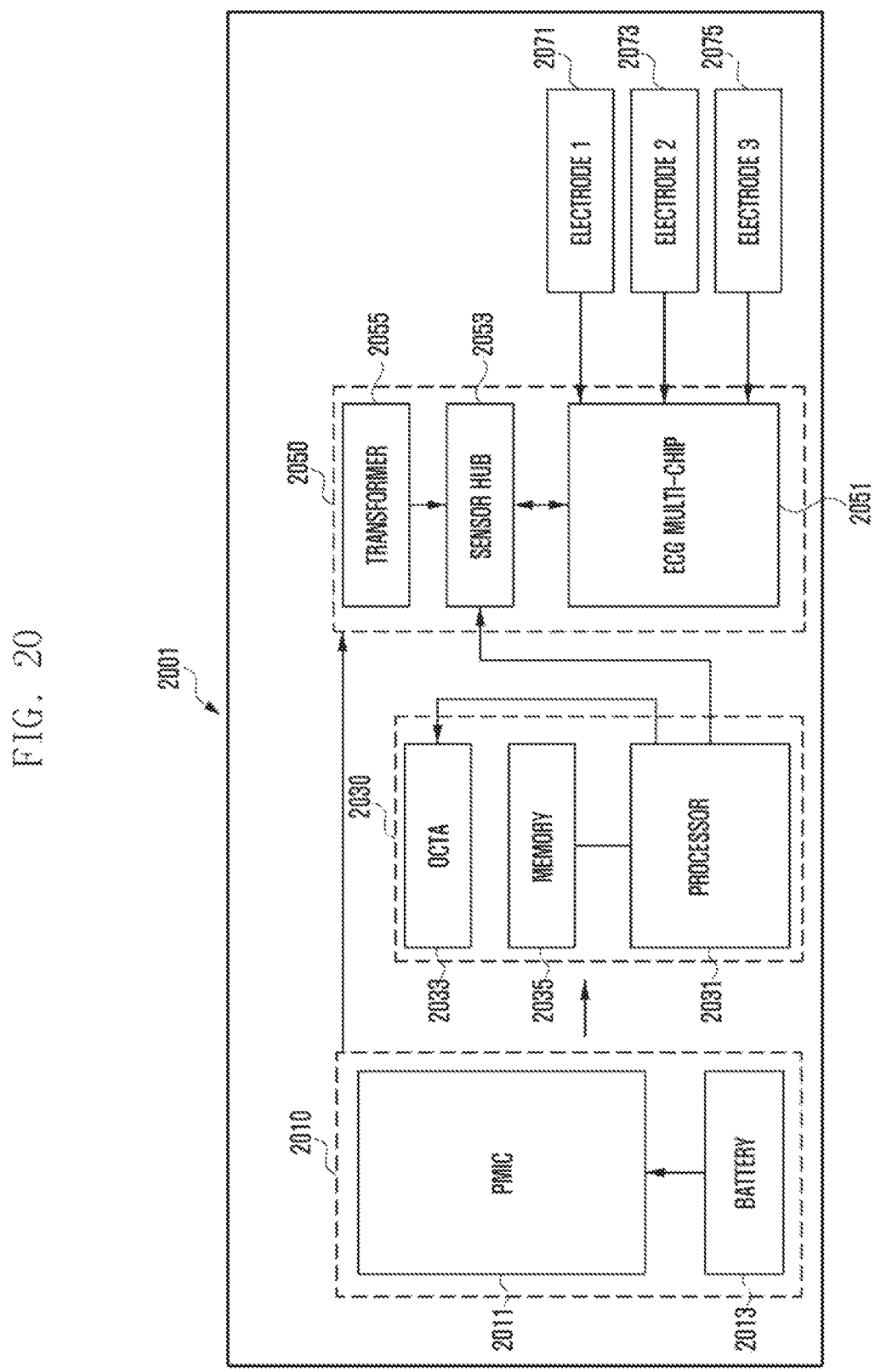
FIG. 20 is a block diagram illustrating an electronic device according to various embodiments of the present disclosure.

FIG. 20 is a block diagram illustrating an electronic device according to various embodiments of the present disclosure.

Referring to FIG. 20, an electronic device 2001 according to various embodiments may include a power supply unit 2010, a processing unit 2030, a signal input unit 2050, a first electrode 2071, a second electrode 2073, and a third electrode 2075.

The power supply unit 2010 can perform a function of supplying power to the processing unit 2030 or the signal input unit 2050. The power supply unit 2010 may include a power management integrated circuit (PMIC) 2011 or a battery 2013. The PMIC 2011, which is a module for managing power use of the electronic device 2001, may have a wired and/or wireless charging scheme. The PMIC may be mounted within, for example, an integrated circuit or an SoC semiconductor. Additionally, the power supply unit 2010 may further include a charger integrated circuit (IC) (not illustrated). The charger IC can charge a battery and can prevent an overvoltage or excess current from being induced or flowing from a charger. According to an embodiment, the charger IC may include a charger IC for at least one of the wired charging scheme and the wireless charging scheme. Examples of the wireless charging may include magnetic resonance charging, magnetic induction charging, and electromagnetic charging, and an additional circuit, such as a coil loop, a resonance circuit, and a rectifier, may be added for the wireless charging.

The battery 2013 can store or generate electricity, and can supply power to the electronic device 801 using the stored or generated electricity. The battery 2013 may include, for example, a rechargeable battery and/or a solar battery.

The processing unit 2030 can perform a function of calculating, storing, displaying or processing information received from the signal input unit 2050. The processing unit 2030 may include a processor 2031, an on-cell touch screen panel (TSP) amoled (OCTA) 2033, or a memory 2035. The processor 2031 can execute calculation or data processing related to control and/or communication of at least one other components of the electronic device 2001. The processor 2031 may include one or more of a central processing unit (CPU), an application processor (AP), and a communication processor (CP). According to various embodiments, the processing 2031 can control a function of calculating, storing, displaying or processing biometric information received from the signal input unit 2050. The AP may be embodied as, for example, a system on chip (SoC). According to an embodiment, the AP may further include a graphic processing unit (GPU).

The OCTA 2033, which is a device having a form in which a display and an input device are mixed, can perform a function of receiving input from a user and displaying information to the user. The OCTA 2033 can display biometric information or health state information processed by the processor 2031.

According to various embodiments, the OCTA 2033 may be replaced with various forms of input devices and display devices included in an input/output interface (not illustrated) and a display (not illustrated). In this case, the input/output interface can, for example, function as an interface that can transfer commands or data input from a user or another external device to the other component(s) of the electronic device. Further, the input/output interface can output commands or data received from the other element(s) of the electronic device to the user or the other external device. The input/output interface can output, through a voice output apparatus such as a speaker or an earphone, voice information corresponding to health state information of a user, which is analyzed through a processor of an electronic device.

The display may include, for example, a liquid crystal display (LCD), a light emitting diode (LED) display, an organic light emitting diode (OLED) display, a micro electro mechanical system (MEMS) display, or an electronic paper display. The display, for example, can display various types of contents (for example, text, images, videos, icons, or symbols) to the user. The display may include a touch screen, and can receive, for example, a touch input, a gesture input, a proximity input, or a hovering using an electronic pen or a body part of the user. According to various embodiments, the display can display the biometric information or the health state information. For example, the display can display an image object, and the like, such as a graph, to correspond to the health state information for a predetermined period of time.

The memory 2035 can perform a function of storing the biometric information or the health state information processed through the processor 2031. The memory 2035 may include an internal memory or an external memory. The internal memory may include, for example, at least one of a volatile memory (for example, a dynamic RAM (DRAM), a static RAM (SRAM), and a synchronous dynamic RAM (SDRAM)), and a non-volatile memory (for example, a one time programmable ROM (OTPROM), a programmable ROM (PROM), an erasable and programmable ROM (EPROM), an electrically erasable and programmable ROM (EEPROM), a mask ROM, a flash ROM, a NAND flash memory, and an NOR flash memory).

According to an embodiment, the internal memory may be a Solid State Drive (SSD). The external memory may further include a flash drive, for example, a compact flash (CF), a secure digital (SD), a micro secure digital (Micro-SD), a mini secure digital (Mini-SD), an extreme Digital (xD), a memory stick, etc. The external memory may be functionally connected to the electronic device 2001 through various interfaces. According to an embodiment, the electronic device 2001 may further include a storage device (or a storage medium) such as a hard disc drive.

The signal input unit 2050 may include an Electrocardiogram multi-chip package (ECG MCP) 2051, a sensor hub 2053, or a transformer 2055. The ECG MCP 2051 may include a plurality of circuits, components, or hardware devices related to ECG measurement. The ECG MCP 2051 can perform processing such as amplifying or converting of biometric information (e.g., biometric potential information) received through the electrodes (e.g., the first electrode 2071, the second electrode 2073, or the third electrode 2075). The sensor hub 2053 can perform a function of collecting and processing information of a plurality of sensors included in the electronic device 2001, except for a specific sensor, and controlling the plurality of sensors. The electronic device 2001 may include a sensor module which can measure a physical quantity or detect an operating state of the electronic device 2001, so as to convert the measured or detected information into an electronic signal. The sensor module may include at least one of a gesture sensor, a gyro sensor, an air pressure sensor, a magnetic sensor, an acceleration sensor, a grip sensor, a proximity sensor, a color sensor (e.g., a red green blue (RGB) sensor), a biometric sensor, a temperature/humidity sensor, an illuminance sensor, and an ultraviolet sensor. Additionally or alternatively, the sensor module may include, for example, an E-nose sensor, an electromyography (EMG) sensor, an electroencephalogram (EEG) sensor, an electrocardiogram (ECG) sensor, an infrared (IR) sensor, an iris sensor, a fingerprint sensor, or the like. The sensor module may further include a control circuit (not illustrated) for controlling one or more sensors included in the sensor module.

The transformer 2055 can perform an insulation function between the processing unit 2030 and the signal input unit 2050. According to an embodiment, the transformer 2055 can separately and physically connect the processing unit 2030 and the signal input unit 2050 using a transformer isolator, thereby preventing an electric shock which can occur when the biometric information (e.g., the biometric potential information) is measured. For example, in connection with the measurement of the biometric information, an electrode configured as a ground electrode may have an effect grounded on the basis of the transformer 2055. According to various embodiments, the entirety or a part of the signal input unit 2050 may be included in the biometric sensor.

The above-described components of the electronic device 2001 represent an embodiment of a module which can measure an ECG. According to various embodiments, the electronic device 2001 can receive the biometric information of a user, for example, biometric potential information through a plurality of electrodes, for example, the first electrode 2071, the second electrode 2073, and the third electrode 2075. The received biometric potential information can be amplified or converted through the ECG MCP 2051. In this case, the sensor hub 2053 can collect and process information of the ECG MCP 2051 and the plurality of electrodes, and control the ECG MCP 2051 and the plurality of electrodes. The sensor hub 2053 can transmit the processed biometric potential information to the processor 2031. The processor 2031 can analyze the biometric potential information transmitted using the biometric potential information stored in the memory 2035, and generate the health state information of the user on the basis of the analyzed biometric potential information. The processor 2031 can make a control to store, in the memory 2035, the transmitted biometric potential information or the generated health state information, and to display the information through the OCTA 2033.

The above described components of the electronic device according to various embodiments of the present disclosure may be formed of one or more components, and a name of a corresponding component element may be changed based on the type of electronic device. The electronic device according to the present disclosure may include one or more of the aforementioned components or may further include other additional components, or some of the aforementioned components may be omitted. Further, some of the components of the electronic device according to the various embodiments of the present disclosure may be combined to form a single entity, and thus, may equivalently execute functions of the corresponding elements prior to the combination.

Examples of computer-readable media include: magnetic media, such as hard disks, floppy disks, and magnetic tape; optical media such as compact disc read only memory (CD-ROM) disks and digital versatile disc (DVD); magneto-optical media, such as floptical disks; and hardware devices that are specially configured to store and perform program instructions (e.g., programming modules), such as read-only memory (ROM), random access memory (RAM), flash memory, etc. Examples of program instructions include machine code instructions created by assembly languages, such as a compiler, and code instructions created by a high-level programming language executable in computers using an interpreter, etc. The described hardware devices may be configured to act as one or more software modules in order to perform the operations and methods described above, or vice versa Modules or programming modules according to the embodiments of the present disclosure may include one or more components, remove part of them described above, or include new components. The operations performed by modules, programming modules, or the other components, according to the present disclosure, may be executed in serial, parallel, repetitive or heuristic fashion. Part of the operations may be executed in any other order, skipped, or executed with additional operations.

Although the present disclosure has been described with an exemplary embodiment, various changes and modifications may be suggested to one skilled in the art. It is intended that the present disclosure encompass such changes and modifications as fall within the scope of the appended claims.

What is claimed is:
1. An electronic device comprising:
a biometric sensor configured to detect at least one contact signal from at least one biometric electrode; and
a processor configured to:
determine whether the at least one contact signal received from the biometric sensor includes biological characteristics,
execute a biometric function in response to a determination that the contact signal is a biometric input including the biological characteristics,
execute an application function of the electronic device in response to a determination that the contact signal is an electrode input when the contact signal does not include the biological characteristics,
identify, when the contact signal does not include the biological characteristics, a position of a biometric electrode in which the contact signal is generated, and
identify the application function mapped to the identified position.
2. The electronic device of claim 1, further comprising:
a comparator configured to detect a voltage change; and
an amplifier configured to amplify the contact signal,
wherein the comparator and the amplifier are connected to the at least one biometric electrode, and
wherein the processor is further configured to:
identify a contact condition based on at least one of the identified position, a contact maintenance time, a number of contact electrodes, an attachment state, or a detachment state,
determine an operation state of the electronic device based on at least one of a locking state of the electronic device, an application operated state of the electronic device, a type of an operating application, or a holding state of the electronic device, and
identify the application function mapped to at least one of the contact condition or the operation state of the electronic device.
3. The electronic device of claim 2, wherein the processor is configured to perform user authentication on the basis of biometric information, permit or change a right of a function of the application when the user authentication is successfully completed, or suppress a right of the function of the application when the user authentication fails, in response to the biometric input in a state in which the user authentication related to the application is required.
4. The electronic device of claim 2, wherein when a condition in which emotional information is required to be measured is satisfied in the application operated state, the processor is configured to generate emotional information on the basis of the biological characteristics in response to the biometric input, and change a function of the operating application to correspond to the generated emotional information or provide the emotional information.
5. The electronic device of claim 2, wherein the processor is configured to trigger activation of an application mapped to each contact condition in response to the electrode input.
6. The electronic device of claim 2, wherein the processor is configured to execute a first function of the application in response to the electrode input based on a contact state of the at least one biometric electrode in a state in which the application is executed, and execute a second function of the application in response to the electrode input based on a contact state change.
7. The electronic device of claim 1, wherein the processor is configured to determine that the contact signal is a biometric signal when it is satisfied that the contact signal is at least one of a signal included in a biometric contact range, a signal included in a determined range generated by the biological characteristics, or a signal including the biological characteristics enabling electrocardiogram (ECG) measurement, and
wherein the processor is configured to determine that the contact signal is the electrode input when it is satisfied that the contact signal is at least one of a signal included in a non-body contact range or a signal by which biometric information cannot be generated on the basis of the contact signal.
8. The electronic device of claim 1, wherein the processor is configured to execute at least one of an operation of generating biometric information according to the biological characteristics, performing user authentication on the basis of the biometric information, unlocking the electronic device when the user authentication is successfully completed, or a function of executing an application related to the biometric information, in response to the biometric input based on the contact signal in a state in which the electronic device is locked.
9. A method of controlling functions of an electronic device, the method comprising:
detecting a contact signal from at least one biometric electrode;

determining whether the contact signal of the at least one biometric electrode includes biological characteristics;

when the contact signal including the biological characteristics is a biometric input, executing a biometric function; and identifying, when the contact signal does not include the biological characteristics, a position of the biometric electrode in which the contact signal is generated, identifying an application function mapped to the position, and executing the identified application function.

10. The method of claim 9, further comprising:

determining that the contact signal includes the biological characteristics when it is satisfied that the contact signal is any one or a combination of a signal included in a biometric contact range, a signal included in a determined range generated by the biological characteristics or a signal including the biological characteristics enabling biological characteristics enabling electrocardiogram (ECG) measurement.

11. The method of claim 9, further comprising:

determining a contact condition based on at least one of the position of a biometric electrode in which the contact signal is generated, a contact maintenance time, a number of biometric electrodes in which contact signals are generated, a biometric attachment state, or a biometric detachment state; and determining an operation state of the electronic device, which is based on at least one of a locking state of the electronic device, an application operated state of the electronic device, a type of an operated application, or a holding state of the electronic device.

12. The method of claim 9, wherein executing the biometric function comprises:

when the biometric input is detected in a state in which the electronic device is locked or user authentication of an application is required, generating biometric information on which biological characteristics are reflected from the contact signal of the at least one biometric electrode;

performing user authentication on the basis of the generated biometric information;

when the user authentication is successfully completed, unlocking the electronic device or permitting or changing a right of a function of the application; and when the user authentication fails, maintaining a locking state or suppressing the right of the function of the application.

13. The method of claim 9, wherein executing the biometric function comprises:

when the biometric input is detected, automatically executing an application related to the biological characteristics on the basis of the biometric input.

14. The method of claim 9, wherein executing the biometric function comprises:

when the biometric input is detected in an application executed state, generating emotional information on the basis of the biological characteristics; and making a change to reflect the emotional information on an executed application by reflecting the generated emotional information, or providing an object indicating the emotional information to an application execution screen.

15. The method of claim 9, wherein executing the application function comprises:

activating a preconfigured application according to each position of a biometric electrode in which the contact signal is generated.

16. The method of claim 9, wherein executing the application function comprises:

when the contact signal is an electrode input based on a contact state of the at least one biometric electrode in an application executed state, executing a first function of the application in response to the electrode input; and when the contact signal is the electrode input based on a change of the contact state, executing a second function of the application in response to the electrode input.

17. A computer program product comprising computer executable program code recorded on a computer readable non-transitory storage medium, said computer executable program code, when executed by an electronic device, causing actions including:

detecting a contact signal from at least one biometric electrode included in the electronic device;

determining whether the contact signal of the at least one biometric electrode includes biological characteristics;

in response to a determination that the contact signal is a biometric input including the biological characteristics, executing a biometric function; and identifying, in response to a determination that the contact signal is an electrode input when the contact signal does not include the biological characteristics, a position of the biometric electrode in which the contact signal is generated, and identifying an application function mapped to the position and executing the identified application function.

* * * * *